United States Patent
Collinson et al.

(10) Patent No.: US 12,226,611 B2
(45) Date of Patent: *Feb. 18, 2025

(54) PRESSURE CONTROL APPARATUS

(71) Applicant: Smith & Nephew PLC, Watford (GB)

(72) Inventors: Sarah Jenny Collinson, Hull (GB); Edward Yerbury Hartwell, Hull (GB); Derek Nicolini, Brough (GB)

(73) Assignee: Smith & Nephew PLC, Watford (GB)

( * ) Notice: Subject to any disclaimer, the term of this patent is extended or adjusted under 35 U.S.C. 154(b) by 913 days.

This patent is subject to a terminal disclaimer.

(21) Appl. No.: 17/339,464

(22) Filed: Jun. 4, 2021

(65) Prior Publication Data
US 2021/0353849 A1 Nov. 18, 2021

Related U.S. Application Data

(63) Continuation of application No. 16/141,701, filed on Sep. 25, 2018, now Pat. No. 11,027,051, which is a (Continued)

(30) Foreign Application Priority Data

Sep. 20, 2010 (GB) ..................................... 1015656

(51) Int. Cl.
*A61M 5/168* (2006.01)
*A61F 13/00* (2024.01)
(Continued)

(52) U.S. Cl.
CPC ......... *A61M 5/16831* (2013.01); *A61F 13/05* (2024.01); *A61M 1/73* (2021.05);
(Continued)

(58) Field of Classification Search
None
See application file for complete search history.

(56) References Cited

U.S. PATENT DOCUMENTS

| | | |
|---|---|---|
| 3,572,340 A | 3/1971 | Lloyd et al. |
| 3,787,882 A | 1/1974 | Fillmore et al. |
| | (Continued) | |

FOREIGN PATENT DOCUMENTS

| | | |
|---|---|---|
| CN | 101378795 A | 3/2009 |
| CN | 101385887 A | 3/2009 |
| | (Continued) | |

OTHER PUBLICATIONS

Annex to the Communication, the Opposition of European Patent No. 2773383, mailed on Sep. 13, 2019, 17 pages.
(Continued)

*Primary Examiner* — Susan S Su
*Assistant Examiner* — Katherine-Ph Minh Pham
(74) *Attorney, Agent, or Firm* — Knobbe, Martens, Olson & Bear, LLP

(57) ABSTRACT

Methods and apparatuses are disclosed for applying negative pressure to a wound site. In some embodiments, the apparatus comprises a source of negative pressure, a processing element, and a memory comprising instructions configured to, when executed on the processing element, cause the apparatus to attempt to generate, via the source of negative pressure, a desired negative pressure at the wound site. If the desired negative pressure has not been generated after a first predetermined period of time, the instructions cause the apparatus to: deactivate the source of negative pressure for a second predetermined period of time, and subsequently attempt to generate the desired negative pressure at the wound site.

23 Claims, 4 Drawing Sheets

Related U.S. Application Data continuation of application No. 15/941,908, filed on Mar. 30, 2018, now Pat. No. 10,105,473, which is a continuation of application No. 14/972,734, filed on Dec. 17, 2015, now Pat. No. 10,058,644, which is a continuation of application No. 14/256,658, filed on Apr. 18, 2014, now Pat. No. 9,220,823, which is a continuation of application No. 13/824,982, filed as application No. PCT/GB2011/051745 on Sep. 16, 2011, now Pat. No. 8,734,425.

(51) Int. Cl.
*A61F 13/05* (2024.01)
*A61M 1/00* (2006.01)
*A61M 39/22* (2006.01)

(52) U.S. Cl.
CPC .............. *A61M 1/74* (2021.05); *A61M 1/743* (2021.05); *A61M 1/75* (2021.05); *A61M 1/80* (2021.05); *A61M 1/90* (2021.05); *A61M 1/96* (2021.05); *A61M 39/22* (2013.01); *A61F 2013/00174* (2013.01); *A61M 1/732* (2021.05); *A61M 1/966* (2021.05); *A61M 1/985* (2021.05); *A61M 2205/15* (2013.01); *A61M 2205/18* (2013.01); *A61M 2205/3344* (2013.01); *A61M 2205/8212* (2013.01)

(56) References Cited

U.S. PATENT DOCUMENTS

| | | |
|---|---|---|
| 3,972,328 A | 8/1976 | Chen |
| 4,015,912 A | 4/1977 | Kofink |
| 4,062,012 A | 12/1977 | Colbert et al. |
| 4,599,052 A | 7/1986 | Langen et al. |
| 4,643,641 A | 2/1987 | Clausen et al. |
| 4,710,165 A | 12/1987 | McNeil et al. |
| 4,969,880 A | 11/1990 | Zamierowski |
| 5,127,388 A | 7/1992 | Cicalese et al. |
| 5,173,033 A | 12/1992 | Adahan |
| 5,222,714 A | 6/1993 | Morinigo et al. |
| 5,238,732 A | 8/1993 | Krishnan |
| 5,291,822 A | 3/1994 | Alsobrooks et al. |
| 5,349,896 A | 9/1994 | Delaney, III et al. |
| 5,358,494 A | 10/1994 | Svedman |
| 5,360,445 A | 11/1994 | Goldowsky |
| 5,391,179 A | 2/1995 | Mezzoli |
| 5,417,743 A | 5/1995 | Dauber |
| 5,449,003 A | 9/1995 | Sugimura |
| 5,449,347 A | 9/1995 | Preen et al. |
| 5,449,584 A | 9/1995 | Banba et al. |
| 5,466,229 A | 11/1995 | Elson et al. |
| 5,492,313 A | 2/1996 | Pan et al. |
| 5,549,584 A | 8/1996 | Gross |
| 5,616,121 A | 4/1997 | McKay |
| 5,634,391 A | 6/1997 | Eady |
| 5,636,643 A | 6/1997 | Argenta et al. |
| 5,645,081 A | 7/1997 | Argenta et al. |
| 5,676,525 A | 10/1997 | Berner et al. |
| 5,685,214 A | 11/1997 | Neff et al. |
| 5,687,633 A | 11/1997 | Eady |
| 5,693,013 A | 12/1997 | Geuder |
| 5,730,587 A | 3/1998 | Snyder et al. |
| 5,743,170 A | 4/1998 | Pascual et al. |
| 5,759,570 A | 6/1998 | Arnold |
| 5,769,608 A | 6/1998 | Seale |
| 5,785,508 A | 7/1998 | Bolt |
| 5,863,184 A | 1/1999 | Juterbock et al. |
| 5,897,296 A | 4/1999 | Yamamoto et al. |
| 5,950,523 A | 9/1999 | Reynolds |
| 6,056,519 A | 5/2000 | Morita et al. |
| 6,068,588 A | 5/2000 | Goldowsky |
| 6,071,267 A | 6/2000 | Zamierowski |
| 6,080,685 A | 6/2000 | Eady |
| 6,102,680 A | 8/2000 | Fraser et al. |
| 6,138,550 A | 10/2000 | Fingar, Jr. et al. |
| 6,142,982 A | 11/2000 | Hunt et al. |
| 6,145,430 A | 11/2000 | Able et al. |
| 6,158,327 A | 12/2000 | Huss |
| 6,162,194 A | 12/2000 | Shipp |
| 6,174,136 B1 | 1/2001 | Kilayko et al. |
| 6,227,825 B1 | 5/2001 | Vay |
| 6,230,609 B1 | 5/2001 | Bender et al. |
| 6,231,310 B1 | 5/2001 | Tojo et al. |
| 6,249,198 B1 | 6/2001 | Clark et al. |
| 6,323,568 B1 | 11/2001 | Zabar |
| 6,327,960 B1 | 12/2001 | Heimueller et al. |
| 6,343,539 B1 | 2/2002 | Du |
| 6,413,057 B1 | 7/2002 | Hong et al. |
| 6,514,047 B2 | 2/2003 | Burr et al. |
| 6,540,490 B1 | 4/2003 | Lilie |
| 6,589,028 B1 | 7/2003 | Eckerbom et al. |
| 6,604,908 B1 | 8/2003 | Bryant et al. |
| 6,618,221 B2 | 9/2003 | Gillis et al. |
| 6,623,255 B2 | 9/2003 | Joong et al. |
| 6,626,891 B2 | 9/2003 | Ohmstede |
| 6,638,035 B1 | 10/2003 | Puff |
| 6,652,252 B2 | 11/2003 | Zabar |
| 6,655,257 B1 | 12/2003 | Meyer |
| 6,673,036 B1 | 1/2004 | Britto |
| 6,685,681 B2 | 2/2004 | Lockwood et al. |
| 6,695,823 B1 | 2/2004 | Lina et al. |
| 6,752,794 B2 | 6/2004 | Lockwood et al. |
| 6,755,807 B2 | 6/2004 | Risk, Jr. et al. |
| 6,756,903 B2 | 6/2004 | Omry et al. |
| 6,764,462 B2 | 7/2004 | Risk, Jr. et al. |
| 6,815,846 B2 | 11/2004 | Godkin |
| 6,823,905 B1 | 11/2004 | Smith et al. |
| 6,877,419 B2 | 4/2005 | Ohrle et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,041,057 B1 | 5/2006 | Faupel et al. |
| 7,108,683 B2 | 9/2006 | Zamierowski |
| 7,128,735 B2 | 10/2006 | Weston |
| 7,151,348 B1 | 12/2006 | Ueda et al. |
| 7,361,184 B2 | 4/2008 | Joshi |
| 7,363,850 B2 | 4/2008 | Becker |
| 7,374,409 B2 | 5/2008 | Kawamura |
| 7,381,859 B2 | 6/2008 | Hunt et al. |
| 7,401,703 B2 | 7/2008 | McMichael et al. |
| 7,447,327 B2 | 11/2008 | Kitamura et al. |
| 7,524,315 B2 | 4/2009 | Blott et al. |
| 7,534,927 B2 | 5/2009 | Lockwood et al. |
| 7,550,034 B2 | 6/2009 | Janse Van Rensburg et al. |
| 7,553,306 B1 | 6/2009 | Hunt et al. |
| 7,569,742 B2 | 8/2009 | Haggstrom et al. |
| 7,615,036 B2 | 11/2009 | Joshi et al. |
| 7,625,362 B2 | 12/2009 | Boehringer et al. |
| 7,670,323 B2 | 3/2010 | Hunt et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,722,582 B2 | 5/2010 | Lina et al. |
| 7,758,555 B2 | 7/2010 | Kelch et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,785,247 B2 | 8/2010 | Tatum et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,909,805 B2 | 3/2011 | Weston |
| 7,910,791 B2 | 3/2011 | Coffey |
| 7,922,703 B2 | 4/2011 | Riesinger |
| 7,927,319 B2 | 4/2011 | Lawhorn |
| 7,964,766 B2 | 6/2011 | Blott et al. |
| 8,007,257 B2 | 8/2011 | Heaton et al. |
| 8,025,052 B2 | 9/2011 | Matthews et al. |
| 8,034,037 B2 | 10/2011 | Adams et al. |

(56) References Cited

U.S. PATENT DOCUMENTS

| | | |
|---|---|---|
| 8,048,046 B2 | 11/2011 | Hudspeth et al. |
| 8,061,360 B2 | 11/2011 | Locke et al. |
| 8,062,272 B2 | 11/2011 | Weston |
| 8,062,273 B2 | 11/2011 | Weston |
| 8,062,331 B2 | 11/2011 | Zamierowski |
| 8,080,702 B2 | 12/2011 | Blott et al. |
| 8,097,272 B2 | 1/2012 | Addison |
| 8,105,295 B2 | 1/2012 | Blott et al. |
| 8,118,794 B2 | 2/2012 | Weston |
| 8,152,785 B2 | 4/2012 | Vitaris |
| 8,162,907 B2 | 4/2012 | Heagle |
| 8,167,869 B2 | 5/2012 | Wudyka |
| 8,186,978 B2 | 5/2012 | Tinholt et al. |
| 8,188,331 B2 | 5/2012 | Barta et al. |
| 8,207,392 B2 | 6/2012 | Haggstrom et al. |
| 8,215,929 B2 | 7/2012 | Shen et al. |
| 8,235,972 B2 | 8/2012 | Adahan |
| 8,241,015 B2 | 8/2012 | Lillie et al. |
| 8,241,018 B2 | 8/2012 | Harr |
| 8,241,261 B2 | 8/2012 | Randolph et al. |
| 8,257,327 B2 | 9/2012 | Blott et al. |
| 8,257,328 B2 | 9/2012 | Augustine et al. |
| 8,267,918 B2 | 9/2012 | Johnson et al. |
| 8,282,611 B2 | 10/2012 | Weston |
| 8,294,586 B2 | 10/2012 | Pidgeon et al. |
| 8,303,552 B2 | 11/2012 | Weston |
| 8,317,774 B2 | 11/2012 | Adahan |
| 8,323,264 B2 | 12/2012 | Weston et al. |
| 8,350,116 B2 | 1/2013 | Lockwood et al. |
| 8,363,881 B2 | 1/2013 | Godkin |
| 8,366,690 B2 | 2/2013 | Locke et al. |
| 8,366,692 B2 | 2/2013 | Weston et al. |
| 8,372,049 B2 | 2/2013 | Jaeb et al. |
| 8,372,050 B2 | 2/2013 | Jaeb et al. |
| 8,398,614 B2 | 3/2013 | Blott et al. |
| D679,819 S | 4/2013 | Peron |
| D679,820 S | 4/2013 | Peron |
| 8,409,157 B2 | 4/2013 | Haggstrom et al. |
| 8,409,159 B2 | 4/2013 | Hu et al. |
| 8,409,160 B2 | 4/2013 | Locke et al. |
| 8,409,170 B2 | 4/2013 | Locke et al. |
| 8,414,519 B2 | 4/2013 | Hudspeth et al. |
| 8,425,478 B2 | 4/2013 | Olson |
| 8,429,778 B2 | 4/2013 | Receveur et al. |
| 8,444,612 B2 | 5/2013 | Patel et al. |
| 8,444,613 B2 | 5/2013 | Svedman et al. |
| 8,449,267 B2 | 5/2013 | Pascual et al. |
| 8,449,509 B2 | 5/2013 | Weston |
| 8,460,255 B2 | 6/2013 | Joshi et al. |
| 8,500,718 B2 | 8/2013 | Locke et al. |
| 8,513,481 B2 | 8/2013 | Gergely et al. |
| 8,540,688 B2 | 9/2013 | Eckstein et al. |
| 8,545,464 B2 | 10/2013 | Weston |
| 8,545,466 B2 | 10/2013 | Andresen et al. |
| 8,569,566 B2 | 10/2013 | Blott et al. |
| 8,579,872 B2 | 11/2013 | Coulthard et al. |
| 8,617,129 B2 | 12/2013 | Hartwell |
| 8,622,981 B2 | 1/2014 | Hartwell et al. |
| 8,628,505 B2 | 1/2014 | Weston |
| 8,641,691 B2 | 2/2014 | Fink et al. |
| 8,646,479 B2 | 2/2014 | Jaeb et al. |
| 8,663,198 B2 | 3/2014 | Buan et al. |
| 8,708,984 B2 | 4/2014 | Robinson et al. |
| 8,715,256 B2 | 5/2014 | Greener |
| 8,734,131 B2 | 5/2014 | McCrone et al. |
| 8,734,425 B2 | 5/2014 | Nicolini |
| 8,764,732 B2 | 7/2014 | Hartwell |
| 8,795,243 B2 | 8/2014 | Weston |
| 8,808,274 B2 | 8/2014 | Hartwell |
| 8,814,841 B2 | 8/2014 | Hartwell |
| 8,827,983 B2 | 9/2014 | Braga et al. |
| 8,829,263 B2 | 9/2014 | Haggstrom et al. |
| 8,834,451 B2 | 9/2014 | Blott et al. |
| 8,843,327 B2 | 9/2014 | Vernon-Harcourt et al. |
| 8,845,603 B2 | 9/2014 | Middleton et al. |
| 8,905,985 B2 | 12/2014 | Allen et al. |
| 8,926,592 B2 | 1/2015 | Blott et al. |
| 8,945,074 B2 | 2/2015 | Buan et al. |
| 8,951,235 B2 | 2/2015 | Allen et al. |
| 8,956,336 B2 | 2/2015 | Haggstrom et al. |
| 8,974,429 B2 | 3/2015 | Gordon et al. |
| 9,012,714 B2 | 4/2015 | Fleischmann |
| 9,061,095 B2 | 6/2015 | Adie et al. |
| 9,067,003 B2 | 6/2015 | Buan et al. |
| 9,084,845 B2 | 7/2015 | Adie et al. |
| 9,127,665 B2 | 9/2015 | Locke et al. |
| 9,180,231 B2 | 11/2015 | Greener |
| 9,199,011 B2 | 12/2015 | Locke et al. |
| 9,199,012 B2 | 12/2015 | Vitaris et al. |
| 9,220,822 B2 | 12/2015 | Hartwell |
| 9,220,823 B2 | 12/2015 | Nicolini |
| 9,314,557 B2 | 4/2016 | Ricci et al. |
| 9,408,954 B2 | 8/2016 | Gordon et al. |
| 9,421,309 B2 | 8/2016 | Robinson et al. |
| 9,446,178 B2 | 9/2016 | Blott et al. |
| 9,506,463 B2 | 11/2016 | Locke et al. |
| 9,518,575 B2 | 12/2016 | Felber |
| 9,629,986 B2 | 4/2017 | Patel et al. |
| 9,681,993 B2 | 6/2017 | Wu et al. |
| 9,737,649 B2 | 8/2017 | Begin et al. |
| 9,877,872 B2 | 1/2018 | Mumby et al. |
| 9,956,325 B2 | 5/2018 | Malhi |
| 10,058,644 B2 | 8/2018 | Nicolini |
| 10,105,473 B2 | 10/2018 | Nicolini |
| 10,143,783 B2 | 12/2018 | Adie et al. |
| 10,307,517 B2 | 6/2019 | Allen et al. |
| 2001/0001278 A1 | 5/2001 | Drevet |
| 2001/0033795 A1 | 10/2001 | Humpheries |
| 2001/0043870 A1 | 11/2001 | Song |
| 2002/0026946 A1 | 3/2002 | McKay |
| 2002/0122732 A1 | 9/2002 | Oh et al. |
| 2002/0164255 A1 | 11/2002 | Burr et al. |
| 2003/0035743 A1 | 2/2003 | Lee et al. |
| 2003/0095879 A1 | 5/2003 | Oh et al. |
| 2003/0099558 A1 | 5/2003 | Chang |
| 2003/0108430 A1 | 6/2003 | Yoshida et al. |
| 2003/0110939 A1 | 6/2003 | Able et al. |
| 2003/0133812 A1 | 7/2003 | Puff et al. |
| 2003/0161735 A1 | 8/2003 | Kim et al. |
| 2003/0162071 A1 | 8/2003 | Yasuda |
| 2003/0175125 A1 | 9/2003 | Kwon et al. |
| 2003/0175135 A1 | 9/2003 | Heo et al. |
| 2003/0230191 A1 | 12/2003 | Ohrle et al. |
| 2004/0005222 A1 | 1/2004 | Yoshida et al. |
| 2004/0021123 A1 | 2/2004 | Howell et al. |
| 2004/0064132 A1 | 4/2004 | Boehringer et al. |
| 2004/0066097 A1 | 4/2004 | Kobayashi et al. |
| 2004/0071568 A1 | 4/2004 | Hyeon |
| 2004/0071572 A1 | 4/2004 | Greter |
| 2004/0115076 A1 | 6/2004 | Lilie et al. |
| 2004/0118460 A1 | 6/2004 | Stinson |
| 2004/0126250 A1 | 7/2004 | Tsuchiya et al. |
| 2004/0155741 A1 | 8/2004 | Godin |
| 2004/0156730 A1 | 8/2004 | Lilie et al. |
| 2004/0163713 A1 | 8/2004 | Schulze et al. |
| 2004/0182237 A1 | 9/2004 | Headley et al. |
| 2004/0189103 A1 | 9/2004 | Duncan et al. |
| 2004/0219059 A1 | 11/2004 | Barringer et al. |
| 2005/0031470 A1 | 2/2005 | Lee |
| 2005/0098031 A1 | 5/2005 | Yoon et al. |
| 2005/0100450 A1 | 5/2005 | Bryant et al. |
| 2005/0110190 A1 | 5/2005 | Giardini et al. |
| 2005/0111987 A1 | 5/2005 | Yoo et al. |
| 2005/0123422 A1 | 6/2005 | Lilie |
| 2005/0124966 A1 | 6/2005 | Karpowicz et al. |
| 2005/0129540 A1 | 6/2005 | Puff |
| 2005/0135946 A1 | 6/2005 | Kang et al. |
| 2005/0142007 A1 | 6/2005 | Lee et al. |
| 2005/0142008 A1 | 6/2005 | Jung et al. |
| 2005/0155657 A1 | 7/2005 | Kach et al. |
| 2005/0163635 A1 | 7/2005 | Berwanger et al. |
| 2005/0209560 A1 | 9/2005 | Boukhny et al. |
| 2005/0251117 A1 | 11/2005 | Anderson et al. |
| 2005/0267402 A1 | 12/2005 | Stewart et al. |

(56) References Cited

U.S. PATENT DOCUMENTS

| | | |
|---|---|---|
| 2005/0271526 A1 | 12/2005 | Chang et al. |
| 2005/0272142 A1 | 12/2005 | Horita |
| 2005/0276706 A1 | 12/2005 | Radue |
| 2006/0009744 A1 | 1/2006 | Erdman et al. |
| 2006/0017332 A1 | 1/2006 | Kang et al. |
| 2006/0018771 A1 | 1/2006 | Song et al. |
| 2006/0019144 A1 | 1/2006 | Hidaka et al. |
| 2006/0024181 A1 | 2/2006 | Kim |
| 2006/0029675 A1 | 2/2006 | Ginther |
| 2006/0039806 A1 | 2/2006 | Becker |
| 2006/0056979 A1 | 3/2006 | Yoo et al. |
| 2006/0056980 A1 | 3/2006 | Yoo et al. |
| 2006/0057000 A1 | 3/2006 | Hyeon |
| 2006/0061024 A1 | 3/2006 | Jung et al. |
| 2006/0073036 A1 | 4/2006 | Pascual et al. |
| 2006/0083623 A1 | 4/2006 | Higgins et al. |
| 2006/0110259 A1 | 5/2006 | Puff et al. |
| 2006/0118190 A1 | 6/2006 | Takehana et al. |
| 2006/0122558 A1 | 6/2006 | Sherman et al. |
| 2006/0191575 A1 | 8/2006 | Naesje |
| 2006/0192259 A1 | 8/2006 | Silverbrook |
| 2006/0210411 A1 | 9/2006 | Hyeon |
| 2006/0216165 A1 | 9/2006 | Lee |
| 2006/0222532 A1 | 10/2006 | Lee et al. |
| 2006/0228224 A1 | 10/2006 | Hong et al. |
| 2006/0245947 A1 | 11/2006 | Seto et al. |
| 2006/0251523 A1 | 11/2006 | Lee et al. |
| 2006/0271020 A1 | 11/2006 | Huang et al. |
| 2006/0282174 A1 | 12/2006 | Haines |
| 2006/0282175 A1 | 12/2006 | Haines et al. |
| 2006/0287632 A1 | 12/2006 | Sarangapani |
| 2007/0014837 A1 | 1/2007 | Johnson et al. |
| 2007/0016152 A1 | 1/2007 | Karpowicz et al. |
| 2007/0032741 A1 | 2/2007 | Hibner et al. |
| 2007/0032762 A1 | 2/2007 | Vogel |
| 2007/0032763 A1 | 2/2007 | Vogel |
| 2007/0040454 A1 | 2/2007 | Freudenberger et al. |
| 2007/0041856 A1 | 2/2007 | Hansen et al. |
| 2007/0052144 A1 | 3/2007 | Knirck et al. |
| 2007/0055209 A1 | 3/2007 | Patel et al. |
| 2007/0078444 A1 | 4/2007 | Larsson |
| 2007/0091614 A1 | 4/2007 | Kaisser et al. |
| 2007/0179460 A1 | 8/2007 | Adahan |
| 2007/0196214 A1 | 8/2007 | Bocchiola |
| 2007/0219532 A1 | 9/2007 | Karpowicz et al. |
| 2007/0225663 A1 | 9/2007 | Watt et al. |
| 2007/0256428 A1 | 11/2007 | Unger et al. |
| 2007/0260226 A1 | 11/2007 | Jaeb et al. |
| 2007/0282283 A1 | 12/2007 | Kaern et al. |
| 2007/0292286 A1 | 12/2007 | Hell et al. |
| 2007/0295201 A1 | 12/2007 | Dadd |
| 2008/0008607 A1 | 1/2008 | Schade et al. |
| 2008/0015526 A1 | 1/2008 | Reiner et al. |
| 2008/0020178 A1 | 1/2008 | Ohrle et al. |
| 2008/0051708 A1 | 2/2008 | Kumar et al. |
| 2008/0082040 A1 | 4/2008 | Kubler et al. |
| 2008/0089796 A1 | 4/2008 | Schade et al. |
| 2008/0094753 A1 | 4/2008 | Brodkin et al. |
| 2008/0110336 A1 | 5/2008 | Cresswell et al. |
| 2008/0125697 A1 | 5/2008 | Gao |
| 2008/0125698 A1 | 5/2008 | Gerg et al. |
| 2008/0191399 A1 | 8/2008 | Chang |
| 2008/0211435 A1 | 9/2008 | Imagawa |
| 2008/0240942 A1 | 10/2008 | Heinrich et al. |
| 2008/0260551 A1 | 10/2008 | Simmons |
| 2008/0267797 A1 | 10/2008 | Hell et al. |
| 2008/0281281 A1 | 11/2008 | Meyer et al. |
| 2008/0306456 A1 | 12/2008 | Riesinger |
| 2008/0310980 A1 | 12/2008 | Ramsdorf et al. |
| 2009/0008306 A1 | 1/2009 | Cicchello et al. |
| 2009/0012441 A1 | 1/2009 | Mulligan |
| 2009/0028733 A1 | 1/2009 | Duwel |
| 2009/0030383 A1 | 1/2009 | Larsen et al. |
| 2009/0030402 A1* | 1/2009 | Adahan ............... A61M 1/962 15/300.1 |
| 2009/0053081 A1 | 2/2009 | Griffiths |
| 2009/0054855 A1 | 2/2009 | Blott et al. |
| 2009/0060750 A1 | 3/2009 | Chen et al. |
| 2009/0071551 A1 | 3/2009 | Chalich |
| 2009/0081049 A1 | 3/2009 | Tian et al. |
| 2009/0087323 A1 | 4/2009 | Blakey et al. |
| 2009/0114293 A1 | 5/2009 | Kanai et al. |
| 2009/0123513 A1 | 5/2009 | Greener |
| 2009/0125004 A1 | 5/2009 | Shen et al. |
| 2009/0129955 A1 | 5/2009 | Schubert |
| 2009/0129986 A1 | 5/2009 | Wimberger-Friedl et al. |
| 2009/0148320 A1 | 6/2009 | Lucas |
| 2009/0149821 A1 | 6/2009 | Scherson et al. |
| 2009/0166411 A1 | 7/2009 | Kramer et al. |
| 2009/0169402 A1 | 7/2009 | Stenberg |
| 2009/0177051 A1 | 7/2009 | Arons et al. |
| 2009/0206778 A1 | 8/2009 | Roh et al. |
| 2009/0234306 A1 | 9/2009 | Vitaris |
| 2009/0270833 A1 | 10/2009 | DeBelser et al. |
| 2009/0299251 A1 | 12/2009 | Buan |
| 2009/0299306 A1 | 12/2009 | Buan |
| 2009/0304534 A1 | 12/2009 | Richter |
| 2009/0312723 A1 | 12/2009 | Blott et al. |
| 2009/0312725 A1 | 12/2009 | Braga |
| 2009/0315684 A1 | 12/2009 | Sacco et al. |
| 2010/0036367 A1 | 2/2010 | Krohn |
| 2010/0042059 A1* | 2/2010 | Pratt ............... A61M 1/96 700/282 |
| 2010/0068820 A1 | 3/2010 | Meathrel et al. |
| 2010/0098566 A1 | 4/2010 | Kang |
| 2010/0125258 A1 | 5/2010 | Coulthard et al. |
| 2010/0126484 A1 | 5/2010 | Skell et al. |
| 2010/0145289 A1 | 6/2010 | Lina et al. |
| 2010/0160881 A1 | 6/2010 | Lin et al. |
| 2010/0191178 A1 | 7/2010 | Ross et al. |
| 2010/0207768 A1* | 8/2010 | Pidgeon ............... A61M 1/784 340/573.1 |
| 2010/0211030 A1 | 8/2010 | Turner et al. |
| 2010/0244780 A1 | 9/2010 | Turner et al. |
| 2010/0249733 A9 | 9/2010 | Blott et al. |
| 2010/0265649 A1 | 10/2010 | Singh et al. |
| 2010/0268179 A1 | 10/2010 | Kelch et al. |
| 2010/0280435 A1 | 11/2010 | Raney et al. |
| 2010/0318071 A1 | 12/2010 | Wudyka |
| 2010/0320659 A1 | 12/2010 | Chen et al. |
| 2011/0000069 A1 | 1/2011 | Ramsdorf et al. |
| 2011/0004172 A1 | 1/2011 | Eckstein et al. |
| 2011/0015587 A1 | 1/2011 | Tumey et al. |
| 2011/0020588 A1 | 1/2011 | Shimizu et al. |
| 2011/0028921 A1 | 2/2011 | Hartwell et al. |
| 2011/0038741 A1 | 2/2011 | Lissner et al. |
| 2011/0043055 A1 | 2/2011 | Chiang |
| 2011/0054423 A1 | 3/2011 | Blott et al. |
| 2011/0071415 A1 | 3/2011 | Karwoski et al. |
| 2011/0077605 A1 | 3/2011 | Karpowicz et al. |
| 2011/0081267 A1 | 4/2011 | McCrone et al. |
| 2011/0098600 A1 | 4/2011 | Matsumura et al. |
| 2011/0103984 A1 | 5/2011 | Santa |
| 2011/0118683 A1 | 5/2011 | Weston |
| 2011/0130712 A1 | 6/2011 | Topaz |
| 2011/0144599 A1 | 6/2011 | Croizat et al. |
| 2011/0169348 A1 | 7/2011 | Park |
| 2011/0171044 A1 | 7/2011 | Flanigan |
| 2011/0176945 A1 | 7/2011 | Drevet |
| 2011/0176946 A1 | 7/2011 | Drevet |
| 2011/0184341 A1 | 7/2011 | Baker et al. |
| 2011/0186765 A1 | 8/2011 | Jaeb et al. |
| 2011/0196321 A1 | 8/2011 | Wudyka |
| 2011/0202220 A1 | 8/2011 | Seta et al. |
| 2011/0205646 A1 | 8/2011 | Sato et al. |
| 2011/0205647 A1 | 8/2011 | Osaka et al. |
| 2011/0224631 A1 | 9/2011 | Simmons et al. |
| 2011/0229352 A1 | 9/2011 | Timmer |
| 2011/0236265 A1 | 9/2011 | Hasui et al. |
| 2011/0236277 A1 | 9/2011 | Lee et al. |
| 2011/0245682 A1 | 10/2011 | Robinson et al. |
| 2011/0251569 A1 | 10/2011 | Turner et al. |
| 2011/0257572 A1 | 10/2011 | Locke et al. |
| 2011/0311379 A1 | 12/2011 | Hale et al. |

(56) References Cited

U.S. PATENT DOCUMENTS

| | | | |
|---|---|---|---|
| 2012/0000208 A1 | 1/2012 | Hon et al. |
| 2012/0008817 A1 | 1/2012 | Grinker et al. |
| 2012/0034109 A1 | 2/2012 | Tout et al. |
| 2012/0046625 A1 | 2/2012 | Johannison |
| 2012/0053543 A1 | 3/2012 | Miau et al. |
| 2012/0160091 A1 | 6/2012 | Dadd et al. |
| 2012/0165764 A1 | 6/2012 | Allen et al. |
| 2012/0177513 A1 | 7/2012 | Lilie et al. |
| 2012/0184930 A1 | 7/2012 | Johannison |
| 2012/0220960 A1 | 8/2012 | Ruland |
| 2012/0232502 A1 | 9/2012 | Lowing |
| 2012/0251359 A1 | 10/2012 | Neelakantan et al. |
| 2012/0259299 A1 | 10/2012 | Ryu et al. |
| 2012/0271256 A1 | 10/2012 | Locke et al. |
| 2012/0289895 A1 | 11/2012 | Tsoukalis |
| 2012/0289913 A1 | 11/2012 | Eckstein et al. |
| 2012/0301341 A1 | 11/2012 | Ota et al. |
| 2013/0017110 A1 | 1/2013 | Villagomez et al. |
| 2013/0042753 A1 | 2/2013 | Becker et al. |
| 2013/0066285 A1 | 3/2013 | Locke et al. |
| 2013/0085462 A1 | 4/2013 | Nip et al. |
| 2013/0090613 A1 | 4/2013 | Kelch et al. |
| 2013/0118622 A1 | 5/2013 | Patzold et al. |
| 2013/0123755 A1 | 5/2013 | Locke et al. |
| 2013/0138054 A1 | 5/2013 | Fleischmann |
| 2013/0144235 A1 | 6/2013 | Augustine et al. |
| 2013/0150814 A1 | 6/2013 | Buan |
| 2013/0165878 A1 | 6/2013 | Heagle |
| 2013/0267917 A1 | 10/2013 | Pan et al. |
| 2013/0274688 A1 | 10/2013 | Weston |
| 2013/0280113 A1 | 10/2013 | Miranda et al. |
| 2013/0296762 A1 | 11/2013 | Toth |
| 2013/0340870 A1 | 12/2013 | Ito et al. |
| 2014/0100516 A1 | 4/2014 | Hunt et al. |
| 2014/0114268 A1 | 4/2014 | Auguste et al. |
| 2014/0127148 A1 | 5/2014 | Derain |
| 2014/0163490 A1 | 6/2014 | Locke et al. |
| 2014/0194835 A1 | 7/2014 | Ehlert |
| 2014/0228791 A1 | 8/2014 | Hartwell |
| 2014/0276487 A1 | 9/2014 | Locke et al. |
| 2014/0316359 A1 | 10/2014 | Collinson et al. |
| 2015/0032035 A1 | 1/2015 | Banwell et al. |
| 2015/0051560 A1 | 2/2015 | Askem |
| 2015/0073363 A1 | 3/2015 | Kelch et al. |
| 2015/0217032 A1 | 8/2015 | Allen et al. |
| 2015/0335798 A1 | 11/2015 | De Samber et al. |
| 2016/0144084 A1 | 5/2016 | Collinson et al. |
| 2016/0166741 A1 | 6/2016 | Nicolini |
| 2016/0319957 A1 | 11/2016 | Jaeb et al. |
| 2018/0221547 A1 | 8/2018 | Nicolini |
| 2019/0167863 A1 | 6/2019 | Adie et al. |
| 2019/0307934 A1 | 10/2019 | Allen et al. |
| 2020/0171217 A9 | 6/2020 | Braga et al. |

FOREIGN PATENT DOCUMENTS

| | | |
|---|---|---|
| CN | 101516431 A | 8/2009 |
| CN | 101616700 A | 12/2009 |
| CN | 101676563 A | 3/2010 |
| CN | 201953601 U | 8/2011 |
| CN | 103221077 A | 7/2013 |
| DE | 102005007016 A1 | 8/2006 |
| EP | 0208395 A1 | 1/1987 |
| EP | 0411564 A2 | 2/1991 |
| EP | 0578999 A1 | 1/1994 |
| EP | 0604953 A1 | 7/1994 |
| EP | 0759521 A1 | 2/1997 |
| EP | 0775825 A2 | 5/1997 |
| EP | 0793019 A2 | 9/1997 |
| EP | 0809028 A2 | 11/1997 |
| EP | 0898076 A1 | 2/1999 |
| EP | 0909895 A2 | 4/1999 |
| EP | 1114933 A2 | 7/2001 |
| EP | 1153218 A1 | 11/2001 |
| EP | 0708620 B1 | 5/2003 |
| EP | 0993317 B1 | 9/2003 |
| EP | 1406020 A2 | 4/2004 |
| EP | 1430588 A2 | 6/2004 |
| EP | 1449971 A1 | 8/2004 |
| EP | 1554737 A1 | 7/2005 |
| EP | 1556942 A1 | 7/2005 |
| EP | 1469580 B1 | 12/2005 |
| EP | 1757809 A1 | 2/2007 |
| EP | 1850005 A1 | 10/2007 |
| EP | 1476217 B1 | 3/2008 |
| EP | 1460270 B1 | 6/2008 |
| EP | 1791579 B1 | 7/2009 |
| EP | 2145636 A2 | 1/2010 |
| EP | 2161448 A1 | 3/2010 |
| EP | 1932481 B1 | 6/2010 |
| EP | 2216573 A1 | 8/2010 |
| EP | 2253353 A1 | 11/2010 |
| EP | 2302127 A1 | 3/2011 |
| EP | 1956242 B1 | 4/2011 |
| EP | 2366721 A1 | 9/2011 |
| EP | 2462908 A1 | 6/2012 |
| EP | 2544642 B1 | 1/2015 |
| EP | 2648668 A4 | 1/2015 |
| EP | 2830555 A1 | 2/2015 |
| EP | 2836711 A1 | 2/2015 |
| EP | 2254612 B1 | 10/2019 |
| FR | 1163907 A | 10/1958 |
| GB | 1039145 A | 8/1966 |
| GB | 1220857 A | 1/1971 |
| GB | 2235877 A | 3/1991 |
| GB | 2273133 A | 6/1994 |
| GB | 2306580 A | 5/1997 |
| GB | 2342584 A | 4/2000 |
| GB | 2418738 A | 4/2006 |
| GB | 2433298 A | 6/2007 |
| JP | 2000105011 A | 4/2000 |
| JP | 2000220570 A | 8/2000 |
| JP | 2000300662 A | 10/2000 |
| JP | 2001241382 A | 9/2001 |
| JP | 2001286807 A | 10/2001 |
| JP | 2006233925 A | 9/2006 |
| JP | 2008183244 A | 8/2008 |
| JP | 2008194294 A | 8/2008 |
| JP | 2010185458 A | 8/2010 |
| JP | 2013514871 A | 5/2013 |
| WO | WO-8707683 A2 | 12/1987 |
| WO | WO-9421312 A2 | 9/1994 |
| WO | WO-9819068 A1 | 5/1998 |
| WO | WO-0000743 A1 | 1/2000 |
| WO | WO-0007653 A1 | 2/2000 |
| WO | WO-0021586 A1 | 4/2000 |
| WO | WO-0022298 A2 | 4/2000 |
| WO | WO-0049968 A2 | 8/2000 |
| WO | WO-0056378 A1 | 9/2000 |
| WO | WO-0061206 A1 | 10/2000 |
| WO | WO-0079154 A2 | 12/2000 |
| WO | WO-0116488 A1 | 3/2001 |
| WO | WO-0179693 A2 | 10/2001 |
| WO | WO-02087058 A1 | 10/2002 |
| WO | WO-02090772 A1 | 11/2002 |
| WO | WO-03057307 A1 | 7/2003 |
| WO | WO-03085810 A1 | 10/2003 |
| WO | WO-03099356 A2 | 12/2003 |
| WO | WO-03101508 A2 | 12/2003 |
| WO | WO-2004007960 A1 | 1/2004 |
| WO | WO-2004081421 A2 | 9/2004 |
| WO | WO-2005001287 A1 | 1/2005 |
| WO | WO-2005009488 A2 | 2/2005 |
| WO | WO-2005123170 A1 | 12/2005 |
| WO | WO-2006046060 A2 | 5/2006 |
| WO | WO-2006052839 A2 | 5/2006 |
| WO | WO-2006058801 A1 | 6/2006 |
| WO | WO-2006059098 A1 | 6/2006 |
| WO | WO-2006062276 A1 | 6/2006 |
| WO | WO-2006069875 A2 | 7/2006 |
| WO | WO-2006069884 A1 | 7/2006 |
| WO | WO-2006069885 A1 | 7/2006 |
| WO | WO-2006092333 A1 | 9/2006 |
| WO | WO-2006111775 A1 | 10/2006 |

(56) References Cited

FOREIGN PATENT DOCUMENTS

| | | |
|---|---|---|
| WO | WO-2006117207 A1 | 11/2006 |
| WO | WO-2006122268 A2 | 11/2006 |
| WO | WO-2007019038 A2 | 2/2007 |
| WO | WO-2007049876 A1 | 5/2007 |
| WO | WO-2007055642 A1 | 5/2007 |
| WO | WO-2007067359 A2 | 6/2007 |
| WO | WO-2007087811 A1 | 8/2007 |
| WO | WO-2007092397 A2 | 8/2007 |
| WO | WO-2007113597 A2 | 10/2007 |
| WO | WO-2008013896 A2 | 1/2008 |
| WO | WO-2008027449 A2 | 3/2008 |
| WO | WO-2008031418 A2 | 3/2008 |
| WO | WO-2008039223 A1 | 4/2008 |
| WO | WO-2008039314 A2 | 4/2008 |
| WO | WO-2008048481 A2 | 4/2008 |
| WO | WO-2008049029 A2 | 4/2008 |
| WO | WO-2008100440 A1 | 8/2008 |
| WO | WO-2008110022 A2 | 9/2008 |
| WO | WO-2008135997 A2 | 11/2008 |
| WO | WO-2008154158 A2 | 12/2008 |
| WO | WO-2009004367 A1 | 1/2009 |
| WO | WO-2009019415 A2 | 2/2009 |
| WO | WO-2009047524 A2 | 4/2009 |
| WO | WO-2009066104 A1 | 5/2009 |
| WO | WO-2009066105 A1 | 5/2009 |
| WO | WO-2009071924 A1 | 6/2009 |
| WO | WO-2009089390 A2 | 7/2009 |
| WO | WO-2009095170 A2 | 8/2009 |
| WO | WO-2009103031 A1 | 8/2009 |
| WO | WO-2009124100 A1 | 10/2009 |
| WO | WO-2009124125 A2 | 10/2009 |
| WO | WO-2009126103 A1 | 10/2009 |
| WO | WO-2009146441 A1 | 12/2009 |
| WO | WO-2009151645 A2 | 12/2009 |
| WO | WO-2009156984 A2 | 12/2009 |
| WO | WO-2009158128 A2 | 12/2009 |
| WO | WO-2010017484 A2 | 2/2010 |
| WO | WO-2010021783 A1 | 2/2010 |
| WO | WO-2010033574 A1 | 3/2010 |
| WO | WO-2010033613 A1 | 3/2010 |
| WO | WO-2010033769 A1 | 3/2010 |
| WO | WO-2010039481 A1 | 4/2010 |
| WO | WO-2010051068 A1 | 5/2010 |
| WO | WO-2010051418 A2 | 5/2010 |
| WO | WO-2010056977 A2 | 5/2010 |
| WO | WO-2010093753 A1 | 8/2010 |
| WO | WO-2010126444 A1 | 11/2010 |
| WO | WO-2010142959 A2 | 12/2010 |
| WO | WO-2010144089 A1 | 12/2010 |
| WO | WO-2010147533 A1 | 12/2010 |
| WO | WO-2011003163 A1 | 1/2011 |
| WO | WO-2011068310 A2 | 6/2011 |
| WO | WO-2011082461 A1 | 7/2011 |
| WO | WO-2011087871 A2 | 7/2011 |
| WO | WO-2011097361 A2 | 8/2011 |
| WO | WO-2011097362 A1 | 8/2011 |
| WO | WO-2011103890 A1 | 9/2011 |
| WO | WO-2011115851 A1 | 9/2011 |
| WO | WO-2011130542 A1 | 10/2011 |
| WO | WO-2011130549 A1 | 10/2011 |
| WO | WO-2011135285 A1 | 11/2011 |
| WO | WO-2011135286 A1 | 11/2011 |
| WO | WO-2011135287 A1 | 11/2011 |
| WO | WO-2011144888 A1 | 11/2011 |
| WO | WO-2011146535 A1 | 11/2011 |
| WO | WO-2011148188 A1 | 12/2011 |
| WO | WO-2011150529 A1 | 12/2011 |
| WO | WO-2012028842 A1 | 3/2012 |
| WO | WO-2012034238 A1 | 3/2012 |
| WO | WO-2012038724 A1 | 3/2012 |
| WO | WO-2012048179 A2 | 4/2012 |
| WO | WO-2012088572 A1 | 7/2012 |
| WO | WO-2012095245 A2 | 7/2012 |
| WO | WO-2012131237 A1 | 10/2012 |
| WO | WO-2012140180 A1 | 10/2012 |
| WO | WO-2012140378 A1 | 10/2012 |
| WO | WO-2012142002 A1 | 10/2012 |
| WO | WO-2012143665 A1 | 10/2012 |
| WO | WO-2013006932 A1 | 1/2013 |
| WO | WO-2013010907 A1 | 1/2013 |
| WO | WO-2013015827 A2 | 1/2013 |
| WO | WO-2013019017 A1 | 2/2013 |
| WO | WO-2013064852 A1 | 5/2013 |
| WO | WO-2013083800 A1 | 6/2013 |
| WO | WO-2013136181 A2 | 9/2013 |
| WO | WO-2013149078 A1 | 10/2013 |
| WO | WO-2014008348 A2 | 1/2014 |
| WO | WO-2014016759 A1 | 1/2014 |
| WO | WO-2014020440 A1 | 2/2014 |
| WO | WO-2014020443 A2 | 2/2014 |
| WO | WO-2014022440 A1 | 2/2014 |
| WO | WO-2014108476 A1 | 7/2014 |
| WO | WO-2014113253 A1 | 7/2014 |
| WO | WO-2015022334 A1 | 2/2015 |
| WO | WO-2015022340 A1 | 2/2015 |

OTHER PUBLICATIONS

Appeal Decision for Japanese Patent Application No. 2013528768, mailed on Jul. 14, 2017, 20 pages.
Brief Communication—Letter from the Opponent, re the Opposition of European Patent No. 2773383, dated Mar. 24, 2021, 4 pages.
Brief Communication—Letter from the Proprietor of the Patent, re the Opposition of European Patent No. 2773383, dated Mar. 24, 2021, 25 pages.
British Standards Institution, "Sterilization of medical devices and packaging," retrieved from URL: https://shop.bsigroup.com/en/Browse-By-Subject/Medical-Device-Standards/Sterilization-of-medical-devices-and-packaging/ onMar. 12, 2020, 1 page.
Communication of further notices of opposition pursuant to Rule 79(2) EPC for the European Patent No. 3146986, mailed on Aug. 20, 2020, 2 pages.
Consolidated List of Cited Opposition Documents of the European Patent No. 2773383, dated Jan. 23, 2020, 1 page.
Decision of Rejection mailed Apr. 4, 2016 for Japanese Application No. 2013-528768, 9 pages.
Diels K., et al., "Leybold Vacuum Handbook, "Pergamon Press, 1966, 10 pages.
European Extended Search Report and Office Action dated Feb. 14, 2017 for European Application No. 16193508.5.
Extent of the Opposition and Request for European Patent No. 3326656, mailed on Feb. 12, 2021, 58 pages.
Information about the result of oral proceedings for European Patent No. 2773383, dated May 19, 2021, 2 pages.
International Preliminary Report on Patentability for Application No. PCT/GB2011/051745, mailed on Mar. 26, 2013, 7 pages.
International Search Report and Written Opinion for Application No. PCT/IB2011/002943, mailed on Jan. 28, 2013, 24 pages.
International Search Report for Application No. PCT/GB2011/051745, mailed on Feb. 2, 2012, 5 pages.
KCI, Inc., "Acti V.A.C. Therapy System," User Manual, Sep. 2007, 64 pages.
KCI Licensing Inc, "Prevena™ Incision Management System," Clinician Guide, Instructions for Use, 390061 Rev C, Nov. 2009, 12 pages .<gdiv class="ginger-extension-definitionpopup" style="left: 525.701px; top: 16.8889px; z-index: 2147483646; display: none;"><gdiv class="ginger-dp">< gdiv class="ginger-dp-content"><gdiv class="ginger-dp-title"><gspan id="dp-title">January</gspan></gdiv>< gdiv class="ginger-dp-description" id="dp-description">the first month of the year; begins 10 days after the winter solstice</gdiv>< gdiv class="ginger-dp-more">More< gspan>(Definitions, Synonyms, Translation)</gspan></gdiv></gdiv></gdiv></gdiv>.
KCI Licensing, Inc., "V.A.C. Via™—Negative Pressure Wound Therapy System," 7-Day V.A.C.® Therapy System, Instructions for Use, 360063 Rev B, Aug. 2010, 24 pages.
KCI to Launch the V.A.C.VIA∩, an Advanced Mobile Healing Technology, dated Apr. 26, 2010, 3 pages.

(56) References Cited

OTHER PUBLICATIONS

KCI USA Inc., "SNAP∩ Therapy System," Instructions for Use, SNAP™ Therapy Cartridge, Jul. 2016, 2 pages.
Kendall ULTEC Hydrocolloid Dressing (4x4"), Product Ordering Page, web page downloaded on Jul. 13, 2014, 1 page.
Kinetic Concepts, Inc. Q2 2010 Earnings Call Transcript, dated Jul. 27, 2010, 25 pages.
Kinetic Concepts Inc., V.A.C. Therapy, dated Jan. 11, 2011, 2 pages.
Letter relating to the Appeal Procedure for the Opposition of the European Patent No. 2618860, mailed on Dec. 23, 2019, 5 pages.
Martin L.H., et al., "A Manual of Vacuum Practice," Melbourne University Press, first published 1947, reprinted 1948, 12 pages.
Matsunaga K., et al., "Gas Permeability of Thermoplastic Polyurethane Elastomers," Polymer Journal, Jun. 2005, vol. 37, No. 6, pp. 413-417.
Morcos A.C., "Voice Coil Actuators & Their Use in Advanced Motion Control Systems," Motion, Jul./Aug. 1995, pp. 25-27.
"SNAP™—Wound Care System," Instructions for Use (L20897), Dec. 9, 2007, 16 pages.
Notice of Communication of amended entries concerning the representative (R. 143(1)(h) EPC) and enclosed letter from the proprietor of the patent dated Jan. 8, 2021 for the European Patent No. 3146986, mailed on Jan. 20, 2021, 6 pages.
Notice of Opposition—Statement of Facts and Arguments for the European Patent No. 2618860, mailed on Aug. 26, 2016, 9 pages.
Notice of Opposition—Statement of Facts and Evidence for the European Patent No. 2773383, dated Dec. 28, 2018, 20 pages.
Notice of Opposition to a European Patent No. 2618860, dated Mar. 16, 2016, 5 pages.
Notice of Reasons for Rejection for Japanese Patent Application No. 2016153604, mailed on Jul. 3, 2017, 4 pages.
Observations filed by Third Party for the European Patent No. 2773383, mailed on Jan. 28, 2020, 7 pages.
Office Action and Search Report mailed Sep. 1, 2015 for Chinese Application No. 201180055731.0, 14 pages.
Office Action mailed Jul. 19, 2016 for Chinese Application No. 201180055731.0, 11 pages.
Office Action mailed Jul. 27, 2015, for Japanese Application No. 2013-528768.
Office Action mailed Apr. 28, 2017 for Canadian Application No. 2811718, 3 pages.
Opponent Arguments for the European Patent No. EP2773383, dated Jan. 28, 2020, 25 pages.
Opponent's Statement of Facts and Arguments for the European Patent No. 3146986, mailed on Jul. 30, 2020, 6 pages.
Opponent Submissions Prior to Oral Proceedings for Opposition to European Patent No. 2618860, dated Sep. 14, 2017, 4 pages.
Opponent's Written Submission in Preparation for the Oral Proceedings, opposition of the European Patent No. 2773383, dated Mar. 16, 2020, 8 pages.
Opposition.Statement of Facts and Evidence for Opposition for the European Patent No. 2618860, filed on Mar. 16, 2016, 9 pages.
Opposition by KCI Licensing Inc. to EP2708216 Smith & Nephew Inc., Submitted as Evidence in Support of tile Appeal re European Patent No. 2618860, dated Apr. 5, 2018, 5 pages.
Oral Proceeding Minutes, Decision Rejecting the Opposition, and Grounds of Decision, re European Patent No. EP2618860, dated Jan. 19, 2018, 11 pages.
Park S.M., et al., "Design and Analysis of VCA for Fuel Pump in Automobile," World of Academy of Science, Engineering and Technology, vol. 80, 2011, pp. 573-576.
Patentee Final Written Submissions in Advance of Oral Proceedings for Opposition to European Patent No. 2618860, dated Sep. 13, 2017, 4 pages.
Preliminary Opinion of the Opposition Division for the European Patent No. 2618860, mailed on Dec. 22, 2016, 5 pages.
Proprietor Arguments for the European Patent No. EP2773383, dated Jan. 28, 2020, 32 pages.
Proprietor Reply to Statement of Opponent's Grounds of Appeal, re European Patent No. 2618860, dated Sep. 28, 2018, 38 pages.
Proprietor's Written Submission in Preparation for the Oral Proceedings, opposition of European Patent No. 2773383, dated Mar. 18, 2020, 9 pages.
Protz K., "Modern Wound Dressings Support the Healing Process," Wound care: Indications and Application, Geriatrie Journal, Apr. 2005, pp. 3333-3339 (17 pages with English translation).
Rangwala A.S., "Reciprocating Machinery Dynamics," New Age International Publishers, ISBN:81-224-1813-9, 2006, 6 pages.
Reply of the Patent Proprietor to the Notice of the Opposition, the Opposition of European Patent No. 2773383, mailed on Jun. 3, 2019, 11 pages.
Smith & Nephew, "Smith & Nephew Introduces the First, Pocket-sized, Canister Free, Portable Negative Wound Therapy System in the EU," Cision PR Newswire press release, May 25, 2011, 4 pages.
Smith & Nephew, "Smith & Nephew Introduces the First, Pocket-sized, Canister Free, Portable Negative Wound Therapy System in the EU," Press Release, May 25, 2011, 3 pages.
Smith & Nephew, "Patient Home Care Information," PICO booklet, Mar. 2011, 12 pages.
Smith & Nephew, "PICO—The Early Studies," Case Study booklet, Mar. 2011, 24 pages.
Smith & Nephew, "PICO Single Use Negative Pressure Wound Therapy System," Spiral Booklet, Jul. 2011, 11 pages .<gdiv class="ginger-extension-definitionpopup" style="left: 405.424px; top: 16.8889px; z-index: 2147483646; display: none;"><gdiv class="ginger-dp"><gdiv class="ginger-dp-content"><gdiv class="ginger-dp-title"><gspan id="dp-title">March</gspan></gdiv><gdiv class="ginger-dp-description" id="dp-description">the act of marching; walking with regular steps (especially in a procession of some kind)</gdiv>< gdiv class="ginger-dp-more">More< gspan>(Definitions, Synonyms, Translation)</gspan></gdiv></gdiv></gdiv></gdiv>.
Smith & Nephew, "Pictures of Pump Assembly of Device Obtained for the application No. 170203441.5," Oct. 28, 2020, 28 pages.
SNAP™ Therapy System, "Monograph," KCI, 3 pages.
Statement of Opponent's Grounds of Appeal for European Patent No. EP2618860, dated May 18, 2018, 4 pages.
Summons to attend oral proceedings pursuant to Rule 115(1) EPC for European Patent No. 2773383, mailed on Sep. 30, 2020, 19 pages.
Summons to attend oral proceedings pursuant to Rule 115(1) EPC for the European Patent No. 3146986, mailed on Apr. 19, 2021, 10 pages.
The Constructor, "Reciprocating Pump—Components, Working and Uses," Retrieved from https://theconstructor.org/practical-guide/reciprocating-pumpcomponents-working-uses/2914/ on Jan. 21, 2020, 4 pages.
Trademark/Service Mark Statement of Use (15 U.S.C. Section 1051(d)) for V.A.C.VIA, dated Sep. 22, 2010, 6 pages.
U.S. Office Action mailed on Aug. 15, 2013 for U.S. Appl. No. 13/824,982, 14 pages.
Wikipedia, "Pump," retrieved from https://en.wikipedia.org/wiki/Pump on Mar. 13, 2020, 11 pages.
Written Submission by the Opponent for Opposition of European Patent No. EP2773383, dated Jul. 22, 2020, 2 pages.
Written Submission by the Proprietor for Opposition of European Patent No. EP2773383, dated Jul. 22, 2020, 15 pages.
Brief Communication—Letter from the opponent of the Patent, re the Opposition for European Patent No. 3146986, dated Feb. 3, 2022, 2 pages.
Brief Communication—Letter from the opponent of the Patent, re the Opposition for European Patent No. 3146986, dated Jan. 26, 2022, 4 pages.
Brief Communication—Letter from the Opponent, re the Opposition of European Patent No. 3326656, dated Oct. 14, 2021, 41 pages.
Brief Communication—Letter from the Proprietor of the Patent, re the Opposition for European Patent No. 3146986, dated Dec. 15, 2021, 7 pages.
Brief Communication—Letter from the Proprietor of the Patent, re the Opposition for Simmons & Simmons for European Patent No. 3146986, dated Feb. 7, 2022, 2 pages.

(56) References Cited

OTHER PUBLICATIONS

Brief Communication of the Opposition Proceedings for European Patent No. 3326656, mailed on Aug. 25, 2021, 34 pages.
Brief Communication of the Opposition Proceedings for European Patent No. 3326656, mailed on Jul. 14, 2022, 11 pages.
Communication pursuant to Rule 82(2) EPC for Application No. 16193508.5, mailed Jun. 14, 2022, 4 pages.
Decision by a different Opposition Division for European Application No. 11802142.7, mailed on Sep. 24, 2021, 22 pages.
Decision by Opposition Division re the Opposition of European Patent No. 2773383, revoking a patent with claims essentially corresponding to the claims presented in the new requests dated Sep. 24, 2021, 22 pages.
Decision revoking the European Patent (Art. 101 (3)(b) EPC) for European Patent No. 2773383, mailed on Sep. 24, 2021, 56 pages.
Dempsey D.J., "Sterilization of Medical Devices: A Review," Journal of Biomaterials Applications, Jan. 1989, vol. 3, pp. 454-523.
Hoxey E., "Sterilization—Regulatory Requirements and Supporting Standards," BSI National Standards Body, Medical Device White Paper Series, Publication Date Unknown, 27 pages.
Interlocutory Decision in Opposition and Accompanying Items for European Patent No. 3146986, mailed on Feb. 23, 2022, 28 pages.
Letter of the Opponent for the European Patent No. 2773383, mailed on Jun. 15, 2022, 57 pages.
Maintenance of the patent with the documents specified in the final decision, re the opposition of European patent No. EP3146986, mailed on Jun. 7, 2022, 1 page.
Opponent's Written Submission in Preparation for the Oral Proceedings, the Opposition of European Patent No. 3146986, dated Dec. 7, 2021, 1 page.
Proprietor's Written Submission in the Opposition Proceedings for European Patent No. 3326656, dated Jul. 13, 2022, 65 pages.
Statement of Grounds of Appeal filed by proprietor for European patent No. 2773383, mailed on Feb. 2, 2022, 53 pages.
Summons to Attend Oral Proceedings pursuant to Rule 115(1) for European Patent No. 3326656, mailed on Dec. 16, 2021, 17 pages.
Termination of the Opposition Proceedings with Maintenance of European Patent No. 3146986, dated Jul. 8, 2022, 1 page.
Summons to Attend Oral Proceedings pursuant to rule 115(1) EPC for Application No. 11802142.7, mailed on Jun. 3, 2020, 20 pages.
Board of Appeal—Letter of the opponent dated May 26, 2023 for European Patent No. 3326656, mailed on Jun. 1, 2023, 60 pages.
Board of Appeal—Letter of the Patent Proprietor dated Dec. 7, 2022 for European Patent No. 2773383, mailed on Dec. 13, 2022, 6 pages.
Boards of Appeal—Letter of the opponent dated Jul. 26, 2024, filed in the opposition against European Patent No. 2773383, mailed on Aug. 1, 2024, 5 pages.
Boards of Appeal—Letter of the Patent Proprietor dated Jun. 7, 2024, filed in the opposition against European Patent No. 2773383, mailed on Jun. 13, 2024, 13 pages.
Brief Communication—Letter from the Opposition Division Aug. 29, 2022, for European Patent No. 3326656, mailed on Aug. 29, 2022, 2 pages.
Brief Communication—Letter of the Opponent of Aug. 19, 2022, for European Patent No. 3326656, mailed on Aug. 24, 2022, 26 pages.
Communication of the Board of Appeal for European Patent No. 2618860, mailed May 4, 2023, 4 pages.
Communication of the Board of Appeal pursuant to Article 15(1) for European Patent No. EP2773383, mailed May 31, 2024, 16 pages.
Information about the Result of Oral Proceedings for European Application No. 17203441.5, mailed on Sep. 13, 2022, 2 pages.
Minutes of Oral Proceedings of Sep. 19, 2024 filed in the opposition against European Patent No. 2773383 mailed on Sep. 25, 2024, 3 pages.
Statement of Grounds of Appeal for European Patent No. 3326656, mailed on Feb. 16, 2023, 125 pages.
Termination of the Opposition Proceedings with Maintenance of European Patent No. 2618860, dated Jul. 3, 2023, 1 page.
Transmittal of decision summons for the Opposition of European Patent No. EP3326656, mailed on Oct. 6, 2022, 27 pages.
Withdrawal of an Appeal—Letter to EPO for European Patent No. 2618860, mailed Jun. 28, 2023, 3 pages.
Decision of Board of Appeal Datasheet for the Decision of Sep. 19, 2024 for European Patent No. 2773383, mailed on Dec. 16, 2024, 25 pages.

\* cited by examiner

PRESSURE CONTROL APPARATUS

CROSS-REFERENCE TO RELATED APPLICATIONS

This application is a continuation of U.S. patent application Ser. No. 16/141,701, filed on Sep. 25, 2018 and issued as U.S. Pat. No. 11,027,051, which is a continuation of U.S. patent application Ser. No. 15/941,908, filed on Mar. 30, 2018 and issued as U.S. Pat. No. 10,105,473, which is a continuation of U.S. patent application Ser. No. 14/972,734, filed on Dec. 17, 2015 and issued as U.S. Pat. No. 10,058,644, which is a continuation of U.S. patent application Ser. No. 14/256,658, filed on Apr. 18, 2014 and issued as U.S. Pat. No. 9,220,823, which is a continuation of U.S. patent application Ser. No. 13/824,982, filed on Jun. 26, 2013 and issued as U.S. Pat. No. 8,734,425, which is a U.S. National Phase application under 35 U.S.C. § 371 of International Application PCT/GB2011/051745, filed Sep. 16, 2011, which claims priority to Great Britain Patent Application No. 1015656.0, filed Sep. 20, 2010. The disclosures of these prior applications are incorporated by reference in their entireties.

BACKGROUND OF THE DISCLOSURE

Field of the Disclosure

The present invention relates to a method and apparatus for applying a negative pressure. In particular, but not exclusively, the present invention relates to the application of a negative pressure to a wound site in the application of topical negative pressure at the wound site.

Background

There is much prior art available relating to the provision of apparatus and methods of use thereof for the application of topical negative pressure (TNP) therapy to wounds together with other therapeutic processes intended to enhance the effects of the TNP therapy. Examples of such prior art include those listed and briefly described below.

TNP therapy (sometimes referred to as Vacuum Assisted Closure or negative pressure wound therapy) assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In International patent application, WO 2004/037334, which is incorporated herein by reference, apparatus, a wound dressing and a method for aspirating, irrigating and cleansing wounds are described. In very general terms, the application describes the treatment of a wound by the application of TNP therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In International patent application, WO 2005/04670, which is incorporated herein by reference, apparatus, a wound dressing and a method for cleansing a wound using aspiration, irrigation and cleansing are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

However, the above described apparatus and methods are generally only applicable to a patient when hospitalised as the apparatus used is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus. To this end GB-A-2 307 180 describes a portable TNP therapy unit which may be carried by a patient and clipped to belt or harness. A negative pressure can thus be applied at a wound site.

However, this portable apparatus is still relatively bulky, and may require monitoring of the patient by a trained caregiver. Furthermore, such portable therapy units commonly have reduced capacity to deal with fluid flow rates into a wound cavity caused by leaks. This leads to a greater number of alarms being raised due to an inability to maintain the desired negative pressure at the wound site in the presence of leaks.

Another problem associated with portable apparatus is that on occasion an onboard power source such as a battery pack is used rather than a continuous connection to a power source such as a mains power source. It will be appreciated that such a battery pack has only a limited power resource and therefore TNP therapy can on occasion be halted prior to a desired moment in time because of power failure.

Another problem associated with therapy units which can be utilised by a patient alone without the need for skilled technical assistants is that from time to time warning lights or warning alarms may be initiated when a desired therapy can not be maintained or initiated. This can be distressing for a patient who may not understand the meaning of the cues.

A still further problem associated with the apparatus used to provide TNP therapy is that from time to time a motor associated with a pump which generates a negative pressure will start up or stop. The change in volume coming from the therapy unit can be a cause of concern to a patient.

SUMMARY OF SOME EXEMPLIFYING EMBODIMENTS

It is an aim of certain embodiments of the present invention to at least partly mitigate one or more of the above-mentioned problems.

It is an aim of certain embodiments of the present invention to provide a method for controlling the provision of a desired negative pressure at a wound site to aid in wound closure and healing.

It is an aim of certain embodiments of the present invention to provide a pressure control apparatus that avoids the generation of unnecessary alarms in the presence of transient leaks.

It is an aim of certain embodiments of the present invention to provide a pressure control apparatus that helps extend battery power lifetime.

It is an aim of certain embodiments of the present invention to provide a pressure control apparatus that reduces a number of pump motor start-up or power down operations.

According to a first aspect of the present invention there is provided apparatus for dressing a wound for the application of topical negative pressure at a wound site, comprising:
  a source of negative pressure;
  a processing element;
  a memory comprising instructions configured to, when executed on the processor, cause the apparatus to perform the steps of:
  via the source of negative pressure, attempting to generate a desired negative pressure at the wound site;
  if the desired negative pressure has not been generated after a first predetermined period of time, deactivating the source of negative pressure for a second predetermined period of time; and
  subsequently attempting to generate the desired negative pressure at the wound site.

According to a second aspect of the present invention there is provided a method of applying topical negative pressure (TNP) at a wound site, comprising the steps of:
  via a source of negative pressure, attempting to generate a desired negative pressure at the wound site;
  if the desired negative pressure has not been generated after a first predetermined period of time, deactivating the source of negative pressure for a second predetermined period of time; and
  subsequently attempting to generate the desired negative pressure at the wound site.

According to a third aspect of the present invention there is provided an apparatus for applying negative pressure to a wound, comprising:
  a source of negative pressure coupled to a dressing; and
  a controller configured to:
    activate the source of negative pressure to generate a first desired negative pressure under the dressing;
    if, upon an expiration of a first time interval, a negative pressure under the dressing has not reached the first desired negative pressure, deactivate the source of negative pressure for a second time interval; and
    upon expiration of the second time interval, activate the source of negative pressure to generate the first desired negative pressure under the dressing.

In some embodiments, the controller is further configured to: deactivate the source of negative pressure when the first desired negative pressure has not been generated under the dressing after activating the source of negative pressure for a first number of times exceeding a first threshold.

In some embodiments, the controller is further configured to: when the first number of times exceeds the first threshold, deactivate the source of negative pressure for a third time interval.

In some embodiments, the apparatus further comprises: a switch configured to signal to the controller to activate or deactivate the source of negative pressure; and the controller is further configured to, upon expiration of the third time interval or upon receiving a signal to activate the source of negative pressure from the switch, activate the source of negative pressure to generate the first desired negative pressure under the dressing.

In some embodiments, the apparatus further comprises: an indicator, wherein the controller is further configured to activate the indicator when the first number of times exceeds the first threshold.

In some embodiments, the controller is further configured to: deactivate the indicator upon expiration of the third time interval or receiving a signal to activate the source of negative pressure from the switch.

In some embodiments, the indicator indicates a leak in the seal.

In some embodiments, the controller is further configured to:
  when the negative pressure under the dressing has reached the first desired negative pressure, deactivate the source of negative pressure and monitor negative pressure under the dressing; and
  if the negative pressure under the dressing drops below a negative pressure threshold, activate the source of negative pressure to generate a second desired negative pressure under the dressing.

In some embodiments, the first and second desired negative pressure are the same.

In some embodiments, the second desired negative pressure is less than the first desired negative pressure.

In some embodiments, the controller is further configured: to deactivate the source of negative pressure if the negative pressure under the dressing has reached the second desired negative pressure or if the negative pressure under the dressing has not reached the second desired negative pressure upon expiration of a fourth time interval.

In some embodiments, if the negative pressure under the dressing has not reached the second desired negative pressure upon expiration of the fourth time interval, the controller is further configured to, upon expiration of the second time interval, activate the source of the negative pressure to generate the first desired negative pressure under the dressing.

In some embodiments, the controller is further configured to: activate the source of the negative pressure to generate the first desired negative pressure under the dressing if the controller has activated the source of negative pressure to reach the second desired negative pressure for a second number of times less than a second threshold.

In some embodiments, the controller is further configured to:
  deactivate the source of negative pressure if the controller has activated the source of negative pressure to reach the second desired negative pressure for the second number of times exceeding the second threshold; and
  upon expiration of the third time interval or upon receiving the signal from the switch to activate the source of negative pressure, activate the source of negative pressure to generate the first desired negative pressure under the dressing.

In some embodiments, the controller is further configured to:
  monitor a duty cycle of the source of negative pressure; and
  deactivate the source of negative pressure if the duty cycle exceeds a first duty cycle threshold without the negative pressure reaching the first or second desired negative pressure under the dressing.

In some embodiments, the duty cycle comprises an amount, proportion, or percentage of time the source of negative pressure is active over a period of time.

In some embodiments, the controller is further configured to: calculate a number of duty cycles that exceed the first duty cycle threshold and deactivate the source of negative pressure when the number of duty cycles that exceed the first duty cycle threshold exceeds a second duty cycle threshold.

In some embodiments, the controller is further configured to calculate a number of consecutive duty cycles that exceed the first duty cycle threshold.

In some embodiments, the second duty cycle threshold comprises 30 minutes.

In some embodiments, the controller is further configured: to upon expiration of the third time interval or upon receiving the signal from the switch to active the source of negative pressure, activate the source of negative pressure to generate the first desired negative pressure under the dressing.

In some embodiments, the source of negative pressure comprises a pump.

In some embodiments, the apparatus further comprises: a pressure sensor configured to sense pressure under the dressing and to communicate the sensed pressure to the controller.

In some embodiments, the apparatus further comprises: a one-way valve coupled between an inlet and the source of negative pressure, wherein the inlet is in fluid communication with the dressing.

In some embodiments, the source of negative pressure comprises: a valve configured to connect the port to an external source of negative pressure.

In some embodiments, the controller is further configured to: activate or deactivate the source of negative pressure by operating the valve.

According to a fourth aspect of the present invention there is provided a method of applying negative pressure to a wound, comprising:
  positioning a dressing over the wound to create a substantially fluid impermeable seal over the wound;
  coupling a source of negative pressure to the dressing;
  activating the source of negative pressure to generate a first desired negative pressure under the dressing;
  if, upon an expiration of a first time interval, a negative pressure under the dressing has not reached the first desired negative pressure, deactivating the source of negative pressure for a second time interval; and
  upon expiration of the second time interval, activating the source of negative pressure to generate the first desired negative pressure under the dressing.

In some embodiments, the method further comprises: deactivating the source of negative pressure when the first desired negative pressure has not been generated under the dressing after activating the source of negative pressure for a first number of times exceeding a first threshold.

In some embodiments, the method further comprises: deactivating the source of negative pressure for a third time interval when the first number of times exceeds the first threshold.

In some embodiments, the method further comprises: activating the source of negative pressure to generate the first desired negative pressure under the dressing upon expiration of the third time interval or upon receiving a signal to activate the source of negative pressure from a switch.

In some embodiments, the method further comprises: indicating to a user when the first number of times exceeds the first threshold.

In some embodiments, the method further comprises: stopping the indication upon expiration of the third time interval or receiving a signal to activate the source of negative pressure from the switch.

In some embodiments, the indicating indicates a leak in the seal.

In some embodiments, the method further comprises:
  when the negative pressure under the dressing has reached the first desired negative pressure, deactivating the source of negative pressure and monitoring negative pressure under the dressing; and
  if the negative pressure under the dressing drops below a negative pressure threshold, activating the source of negative pressure to generate a second desired negative pressure under the dressing.

In some embodiments, the first and second desired negative pressure are the same.

In some embodiments, the second desired negative pressure is less than the first desired negative pressure.

In some embodiments, the method further comprises: deactivating the source of negative pressure if the negative pressure under the dressing has reached the second desired negative pressure or if the negative pressure under the dressing has not reached the second desired negative pressure upon expiration of a fourth time interval.

In some embodiments, the method further comprises: if the negative pressure under the dressing has not reached the second desired negative pressure upon expiration of the fourth time interval, activating the source of the negative pressure to generate the first desired negative pressure under the dressing upon expiration of the second time interval.

In some embodiments, the method further comprises: activating the source of the negative pressure to generate the first desired negative pressure under the dressing if the source of negative pressure has been activated to reach the second desired negative pressure for a second number of times less than a second threshold.

In some embodiments, the method further comprises:
  deactivating the source of negative pressure if the source of negative pressure has been activated to reach the second desired negative pressure for the second number of times exceeding the second threshold; and
  upon expiration of the third time interval or upon receiving the signal from the switch to activate the source of negative pressure, activating the source of negative pressure to generate the first desired negative pressure under the dressing.

In some embodiments, the method further comprises:
  monitoring a duty cycle of the source of negative pressure; and
  deactivating the source of negative pressure if the duty cycle exceeds a first duty cycle threshold without the negative pressure reaching the first or second desired negative pressure under the dressing.

In some embodiments, the duty cycle comprises an amount, proportion, or percentage of time the source of negative pressure is active over a period of time.

In some embodiments, the method further comprises: calculating a number of duty cycles that exceed the first duty cycle threshold and deactivating the source of negative pressure when the number of duty cycles that exceed the first duty cycle threshold exceeds a second duty cycle threshold.

In some embodiments, the method further comprises: calculating a number of consecutive duty cycles that exceed the first duty cycle threshold.

In some embodiments, the second duty cycle threshold comprises 30 minutes.

In some embodiments, the method further comprises: upon expiration of the third time interval or upon receiving the signal from the switch to active the source of negative pressure, activating the source of negative pressure to generate the first desired negative pressure under the dressing.

In some embodiments, the source of negative pressure comprises a pump.

In some embodiments, the method further comprises sensing pressure under the dressing.

In some embodiments, the method further comprises: activating or deactivating the source of negative pressure by operating a valve.

Certain embodiments of the present invention provide the advantage that the raising of alarms due to transient leaks into a wound chamber can be avoided, while also reducing the potential for drawing contaminants into a wound site through a leak into the wound chamber.

Certain embodiments of the present invention provide the advantage of extending the useful life of a battery powered source of negative pressure used to provide a desired negative pressure to a wound site.

BRIEF DESCRIPTION OF THE DRAWINGS

Embodiments of the present invention will now be described hereinafter, by way of example only, with reference to the accompanying drawings in which.

In the drawings like reference numerals refer to like parts.

DETAILED DESCRIPTION OF SOME EXEMPLIFYING EMBODIMENTS

Figure 1:
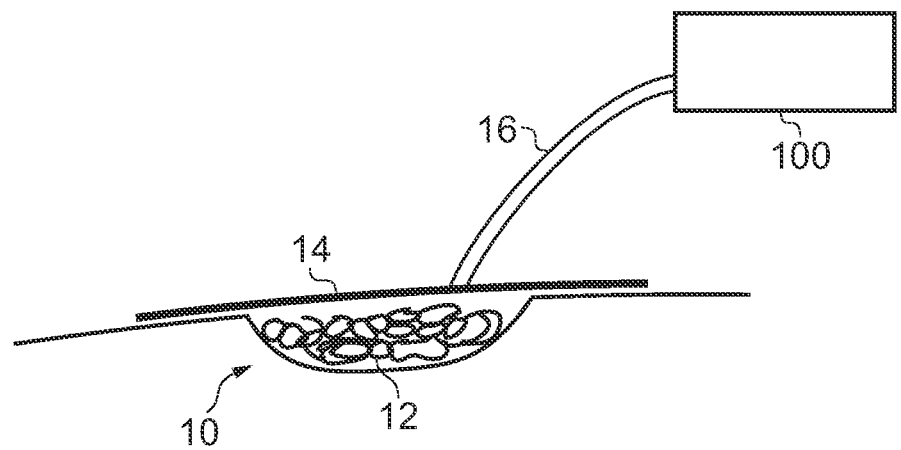
FIG. 1 illustrates an arrangement for applying negative pressure wound therapy to a wound site.

FIG. 1 illustrates an arrangement for applying negative pressure wound therapy to a wound site 10. A packing material 12 is placed within a wound cavity, and then a drape 14 sealed to the surface of the skin around the wound site 10 forming a fluid tight seal around the perimeter of a wound chamber. A source of negative pressure, such as a pressure control apparatus 100 is coupled to the wound cavity via a tube 16. A fluid collection canister (not shown) may be coupled between the pressure control apparatus 100 and the wound chamber to collect any wound exudate drawn from the wound site 10. The use of the packing material 12 is optional, and it may be omitted in certain arrangements as appropriate.

Alternatively, a self contained wound dressing may be used in place of the drape, such a wound dressing absorbs wound exudate within the layers of the dressing removing the need for a separate fluid collection canister.

Further details regarding wound dressings that may be used in combination with the embodiments described herein are found in U.S. application Ser. No. 13/092,042, filed Apr. 21, 2011, the entirety of which is hereby incorporated by reference.

It is envisaged that the negative pressure range for the apparatus in certain embodiments of the present invention may be between about −50 mmHg and −200 mmHg (note that these pressures are relative to normal ambient atmospheric pressure thus, −200 mmHg would be about 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

Figure 2:
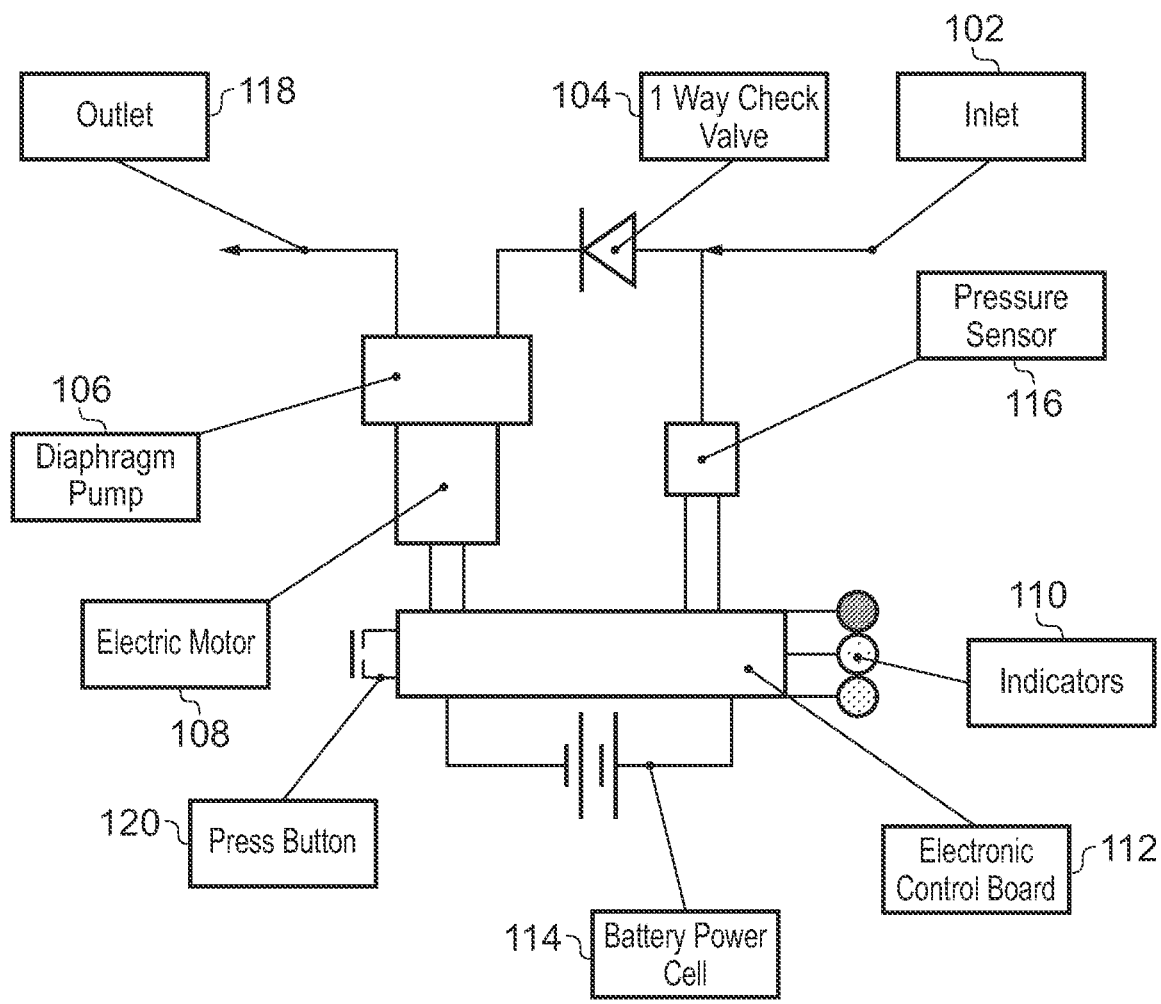
FIG. 2 illustrates a schematic representation of a pressure control apparatus.

FIG. 2 illustrates a schematic representation of a pressure control apparatus 100 according to embodiments of the invention that can be used to apply negative pressure to a wound site 10. The pressure control apparatus includes an inlet 102 coupled to a pressure sensor 116, and also to an inlet of a pump 106 via a one-way check valve 104. The pump is operated by an electric motor 108, which draws power from a battery 114. A controller 112 is coupled to the pressure sensor 116 and provides control signals for controlling the operation of the electric motor 108. Indicators 110 are coupled to the controller 112 to allow audio and/or visual feedback of status signals to a user. An outlet of the pump 106 is coupled to an outlet 118 of the pressure control apparatus. A user can utilise a power button 120 to initiate or terminate operation.

The pump 106 shown is a diaphragm pump which may be highly efficient and capable of providing the required negative pressure. It will be appreciated that other types of pump such as peristaltic pumps, or the like can be used. In some arrangements, the one-way check valve 104 may form part of the pump 106, and may not exist as a separate element of the apparatus.

While the apparatus has been described as being battery powered, it will be understood that the apparatus could alternatively draw electrical power from a mains power supply and the battery power cell removed. In some arrangements, the apparatus may be capable of being powered from either a mains power supply or a rechargeable battery that may be recharged from the mains power supply.

In operation, the inlet 102 is coupled to a wound chamber formed over a wound site 10, for example via the length of tube 16. The electric motor 108 drives the pump 106 under the control of the controller 112 to provide a negative pressure at the inlet 102. The negative pressure can then be communicated to the wound chamber in order to provide a desired negative pressure at the wound site. The check valve 104 maintains the level of negative pressure at the inlet 102 when the pump 106 is not active and helps avoid leaks.

Upon initially connecting the pressure control apparatus 100 to the wound chamber, the pressure at the wound site will be equal to atmospheric pressure, and an initial pump-down must be performed to establish the desired negative pressure at the wound site. This may require the pump 106 to be operated for an extended period of time until the desired negative pressure is achieved.

The pressure at the inlet 102 is indicative of the pressure experienced at the wound site, and this pressure is measured by the pressure sensor 116. The controller 112 receives the pressure value measured at the pressure sensor 116, and once the measured pressure reaches the desired negative pressure, the controller deactivates the pump 106. The controller 112 then continues to monitor the pressure at the pressure sensor.

If during the initial pump-down phase, the controller 112 determines that the desired negative pressure has not been achieved within a certain time (for example 10 minutes or 20 minutes or 30 minutes or 40 minutes or the like), then leaks may be present into the wound chamber, and this condition is signalled via the indicators 110 to show that the wound chamber has not been correctly sealed, or some other error or fault is present.

Once the desired negative pressure has been established, the controller 112 monitors the pressure at the inlet of the pressure control apparatus. From time to time, leaks of fluid may occur into the wound chamber, reducing the level of negative pressure experienced at the wound site, or in other words increasing the absolute pressure at the wound site. The pressure value measured at the pressure sensor 116 and provided to the controller 112 will therefore increase as fluid leaks into the wound chamber. When the measured negative pressure value drops below a certain defined pressure level, the controller 112 will reactivate the pump 106 in order to re-establish the desired negative pressure at the wound site. The desired negative pressure and the defined pressure level at which the controller reactivates the pump provide hysteresis limits between which the pressure should be maintained to apply topical negative pressure to the wound site.

However, if a leak forms that allows fluid, for example air, to leak into the wound chamber with a flow rate greater than the maximum pump capacity 106, it will not be possible for the pressure control apparatus 100 to maintain the desired negative pressure at the wound site. If the pressure control apparatus 100 continued to attempt to re-establish the desired negative pressure in the presence of such a leak, the battery power cell 114 would become depleted. Furthermore, continued operation of the pump in the presence of a large leak can draw contaminants into the wound site, and lead to excessive drying of the wound site which is undesirable. Therefore, the controller 112 is configured to deactivate the pump 106 if the desired negative pressure is not re-established after operation of the pump 106 for a predetermined period of time. For example sometime between around 30 minutes and 4 hours.

The formation of leaks into the wound chamber may occur due to a range of factors. One common cause of such leaks is movement of a patient being treated with the pressure control apparatus 100. For example, a leak may form when a patient moves from a lying to a sitting position, or during the normal range of movement when walking. Such leaks may be transient, and have been found to regularly reseal as the patient continues to move or returns to their previous position. Thus, there is a risk that the pump 106 may be deactivated due to the detection of a leak that subsequently reseals. However, once the leak reseals, operation of the pressure control apparatus would be able to re-establish the desired negative pressure within the wound chamber.

According to embodiments of the invention, the controller 112 is configured to deactivate the pump 106 after the pump has operated for a certain period of time without the desired level of negative pressure being reached in the wound chamber. That is a timeout event occurs. The controller then waits for a further period of time before a retry attempt is made to re-establish the desired negative pressure at the wound site using the pump 106. If the leak has resealed while the pump has been temporarily deactivated, the retry attempt to re-establish the desired negative pressure will be successful, and operation of the pressure control apparatus 100 can continue as normal. However, if the leak is still present a further timeout event will occur and the pump will be deactivated for the further period of time.

This cycle of deactivating the pump 106 and then attempting to re-establish the desired negative pressure may be repeated a number of times in order to provide an opportunity for any leaks to reseal. However, once a timeout event occurs the negative pressure at the wound site will start to degrade, and therefore there will be a break in the negative pressure wound therapy applied to the wound site. While a short break in therapy may not be a concern, an extended period in which the negative pressure is not applied should preferably be avoided. Furthermore, if a leak path into the wound chamber exists for an extended period of time, the potential for contaminants reaching the wound site increases. Thus, if a number, N, of unsuccessful attempts are made to re-establish the desired negative pressure it can be assumed that the leak is permanent, and not transient, and the controller 112 disables operation of the pressure control apparatus 100 and provides a signal via an audio and/or visual cue to a user that attention is required. This allows a patient or caregiver to arrange for any dressings or drapes to be changed to thereby reform the wound chamber and allow the negative pressure wound therapy to be continued. Aptly N is an integer between 1 and 5 inclusive.

Figure 3:
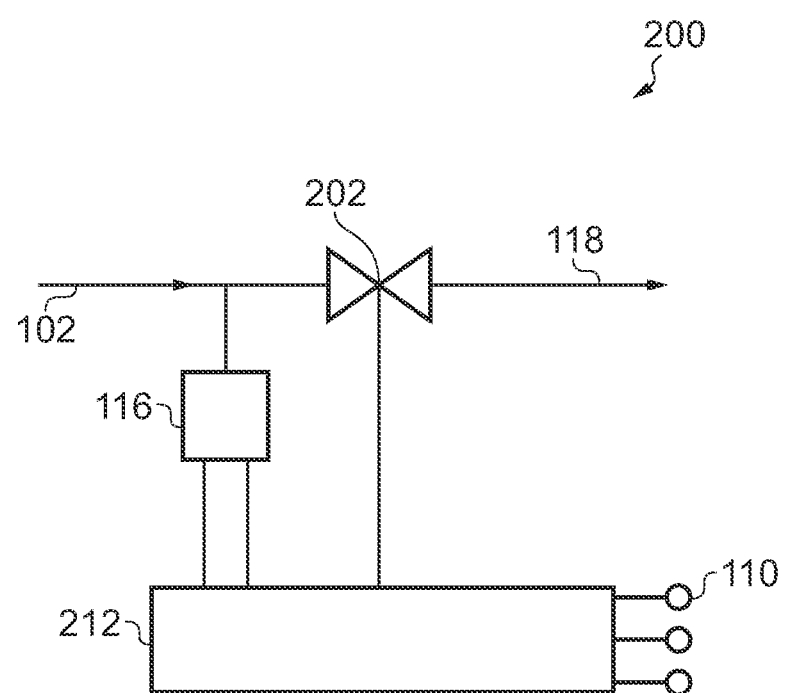
FIG. 3 illustrates a schematic representation of a further pressure control apparatus.

Alternatively, the pump 106 and motor 108 may be omitted, and the negative pressure may be provided via an external source of negative pressure, such as by connection to a vacuum line or vacuum reservoir. FIG. 3 provides a schematic representation of a further pressure control apparatus 200 for use with an external source of negative pressure, and which can be used to provide negative pressure to a wound site 10. Pressure control apparatus 200 includes a controllable valve 202 coupled between an inlet 102 and an outlet 118. The outlet 118 is coupled to the external source of negative pressure. Controller 212 provides control signals to the valve 202 to control the coupling of the external source of negative pressure to the inlet 102, and thereby to the wound chamber. The pressure at the inlet 102 is monitored by a pressure sensor 116, coupled to the inlet, and this monitored pressure is supplied to the controller 212.

The operation of the pressure control apparatus 200 of FIG. 3 is similar to that of the pressure control apparatus 100, except that pressure is controlled by operating the valve 202 to couple the wound chamber to the external source of negative pressure. Controller 112 is able to control the level of negative pressure at the inlet 102 by controlling the valve 202. By monitoring the pressure at the inlet via the pressure sensor 116, the controller 212 can control the valve to provide the desired negative pressure at the wound site.

Unlike the pressure control apparatus of FIG. 2, an extended attempt to provide the desired negative pressure in the presence of a leak will not lead to depletion of a battery power cell. However, longterm it is still undesirable to continue to apply a negative pressure in the presence of a leak due to the possibility of drawing contaminants into the wound chamber, and of drying out the wound site due to the flow of air through the chamber. Thus, the controller 212 of FIG. 3 implements the same control flow as described above with respect to the pressure control apparatus 100. That is, controller 212 is configured to de-couple the inlet 102 from the external source of negative pressure by closing the valve if the desired negative pressure is not established at the wound site within a predetermined period of time. A number of attempts may then be made to re-establish the desired negative pressure in order to provide the opportunity for transient leaks into the wound chamber to reseal.

Thus, the pressure control apparatus of FIGS. 2 and 3 are able to control the application of negative pressure to a wound site, and advantageously reduce the number of alarms due to transient leaks of fluid into the wound chamber. When a leak forms that allows air into the wound chamber at a flow rate above a certain level, the pressure control apparatus is configured to disable the provision of negative pressure to the wound chamber for a predetermined period of time, providing an opportunity for the leak to reseal. Then, if the leak is transient and reseals, the desired negative pressure may then be re-established at a subsequent attempt. This avoids the need to indicate an alarm condition for transient leaks, and also avoids the problem of drawing contaminants and excessive amounts of air into the wound chamber. This also avoids a pump motor being repeatedly energised and de-energised which avoids concerning noise level changes and helps improve pump motor longevity.

Controller 112, 212 may be implemented as a microcontroller, or an application specific integrated circuit, or the like, and may execute instructions to provide the above described control functions. For example, a suitable microcontroller would be one from the STM8L MCU family from ST Microelectronics, for example ST Microelectronics STM8L151G4U6, or one from the MC9S08QE4/8 series from Freescale, such as the Freescale MC9S08QE4CWJ.

The operation of the controller 112 may be described as a finite state machine. The operation of the controller is described below with reference to FIG. 4 which shows a state diagram 300 describing the operation of the controller 112 for the pressure control apparatus shown in FIG. 1.

Figure 5:
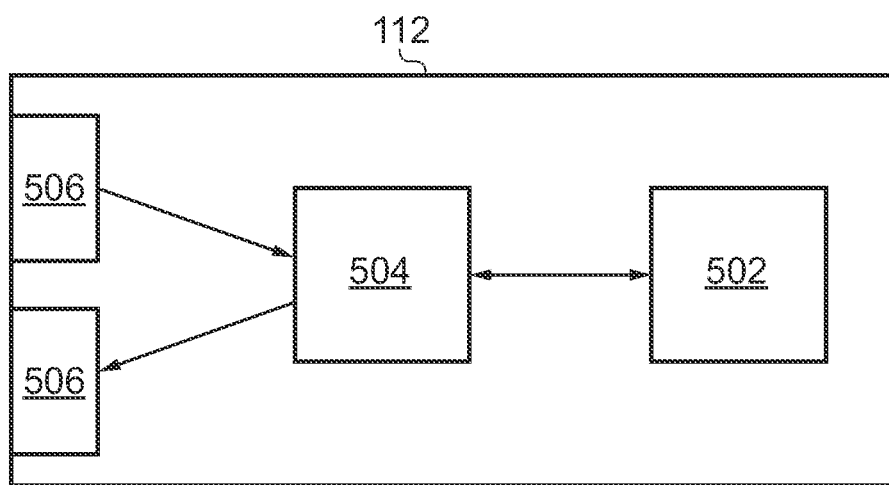
FIG. 5 illustrates a controller.

FIG. 5 illustrates one embodiment of controller 112. The controller comprises a memory 502, which may hold program code for implementing the control functions. The memory is coupled to a microcontroller 504 able to execute the instructions. The microcontroller is coupled to inputs 506 and outputs 508 through which the microcontroller is able to monitor the operation of the system and provide control signals to other parts of the pressure control apparatus.

Referring again to FIG. 4 upon activation 310 of the pressure control apparatus 100 which may occur when an activation strip is pulled for the first time or a user button is pressed or the like, the controller 112 performs a power-on self test (POST) 302 to ensure that the pressure control apparatus is operating correctly. If the power-on self test is failed the pressure control apparatus should not be used. Therefore, after a failed POST, the controller transitions to a non-recoverable error state 304 and the error is signalled to the user via indicators 110. If the POST is passed, the controller 112 transitions to an operational state 308 via a standby state, and performs an initial pump down 312 when a user indicates via a button, in which the pump 106 is operated until a desired negative pressure is established in the wound chamber. Alternatively, the controller may wait on a user input before performing the initial pump-down in state 312.

Once the desired negative pressure has been successfully established, the controller transitions to the monitor pressure state 316. However, if after a predetermined period of time the desired pressure has not been established and the initial pump down state 312 is unable to establish the desired negative pressure (indicative of a leak), a timeout occurs. On the first timeout, the controller will transition to a wait state 314, in which the controller waits for a period of time before transitioning back to the initial pump down state 312. Further timeouts may occur from the initial pump-down state 312, and the controller maintains a count of the number of retry attempts made. Once the desired negative pressure has been established, the number of retry attempts may be reset.

If a timeout occurs and the number of retry cycles is greater than a predefined maximum number of retry attempts allowed, the controller transitions to a paused state 306. While in the paused state 306 the controller will transition from the paused state 306 to the initial pump down state 312 in response to a user input, or after a maximum pause time.

In the monitor pressure state 316, the controller monitors the pressure measured at the pressure sensor 116 and, if the pressure drops out of the desired pressure range, the controller transitions to a maintenance pump-down state 318. In the maintenance pump-down state 318, the suction pump is activated either for a predetermined period of time, for example between around 10 and 60 seconds, or until the desired negative pressure is re-established in the wound chamber, whichever occurs sooner.

It is noted that some hysteresis is built into the desired pressure range, such that the pressure value, a minimum desired negative pressure, that triggers a transition from the monitor pressure state 316 to the maintenance pump-down state 318 is lower than the desired negative pressure established in the wound chamber by operation of the pump during the maintenance pump-down state 318. For example, taking the operating pressure ranges discussed above, the desired negative pressure may be −150 mmHg and the minimum desired negative pressure may be −75 mmHg. Alternatively, the controller may act to maintain the pressure within a certain percentage range of the desired negative pressure, for example a 5% hysteresis may be used.

If the desired negative pressure is reached before the suction pump has been operating for the predetermined period of time, the controller transitions back to the monitor pressure state 316.

However, if the pump operates for the predetermined period of time without the desired negative pressure being re-established in the wound chamber, normally due to a leak into the wound chamber, the pressure control apparatus will signal the presence of a leak. If the pressure is within the hysteresis limits, i.e. between the minimum desired negative pressure and the desired negative pressure, this signifies the presence of a high leak, having a flow rate similar to the capacity of the pump. In this situation, the pump continues to operate until the desired negative pressure is re-established, or until the pressure at the wound site is no longer held within the hysteresis limits.

If in the presence of a large leak, the desired negative pressure is restored before a maximum maintenance time is reached, the controller will transition back to the monitor pressure state 316, but will signal the presence of a leak. However, if the suction pump is operated for more than the maximum maintenance time to restore the desired negative pressure, the controller will transition to the paused state 306, while signalling the presence of a leak.

If during the maintenance pump-down state 318, the pressure in the wound chamber is not maintained within the hysteresis limits, a catastrophic leak has occurred, and the controller transitions to the wait state 314.

In some embodiments, if after a predetermined period of time, the desired pressure has not been established and the maintenance pump down state 318 is unable to establish the desired negative pressure before the maximum maintenance time is reached, a timeout occurs. On the first timeout, the controller will transition to the wait state 314, in which the controller waits for a period of time before transitioning back to the initial pump down state 312. Further timeouts may occur from the maintenance pump-down state 318, and the controller maintains a count of the number of retry attempts made. Once the desired negative pressure has been established in the maintenance pump down state 318, the number of retry attempts may be reset. If a timeout occurs and the number of retry attempts is greater than a predefined maximum number of retry attempts allowed, the controller transitions to the paused state 306, as described above.

Figure 4:
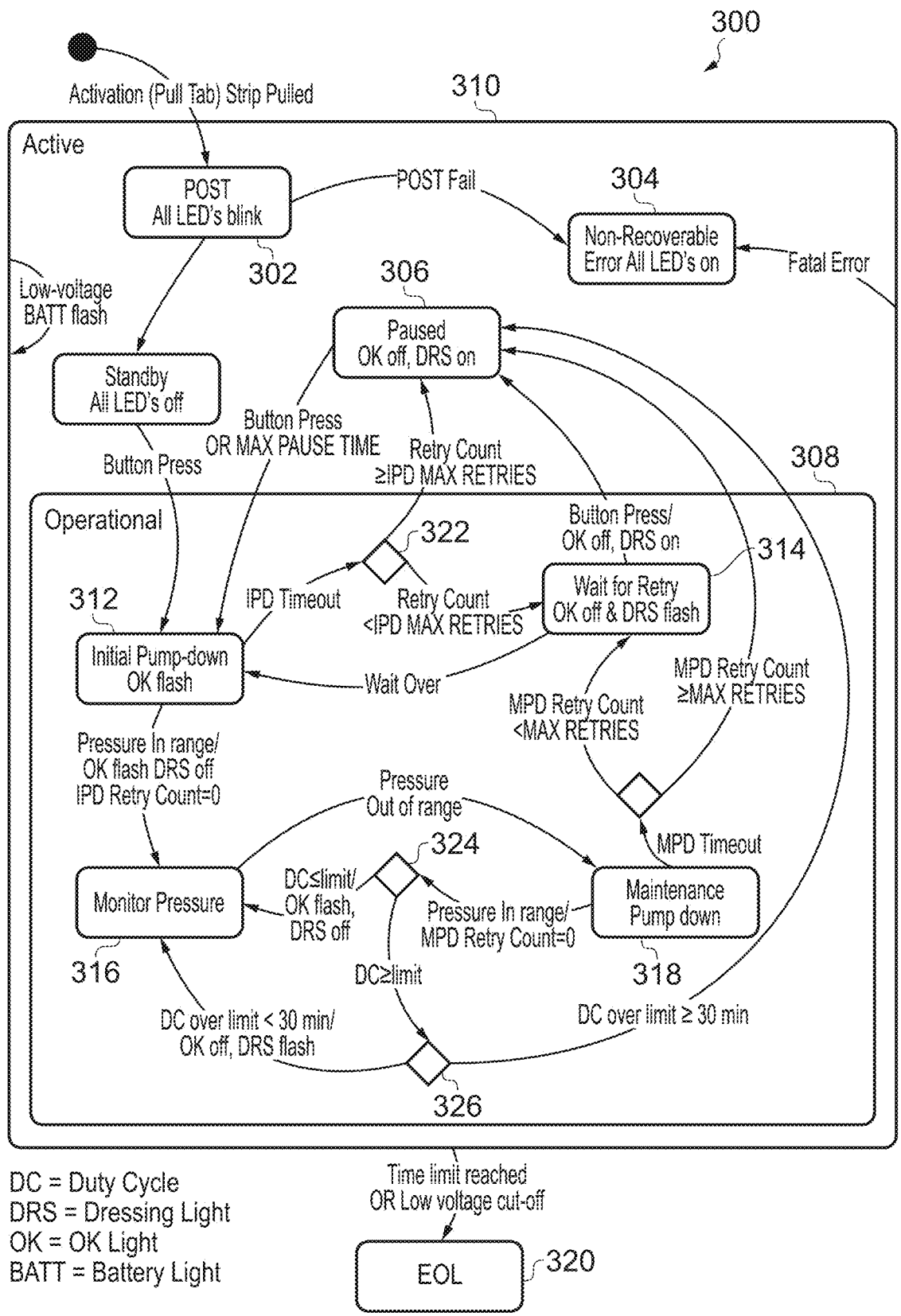
FIG. 4 illustrates a state diagram of a controller.

Thus, if the leak is such that it is over a prescribed limit and the pump duty cycle (DC) as defined, in some embodiments, as pump on time divided by pump off time is over a predetermined limit then the pump shall continue to operate within the hysteresis limits for a particular time duration. For example, around 30 minutes as shown in FIG. 4. Thus, in the monitor pressure loop if the duty cycle is less than a predetermined limit then all is okay. If the duty cycle is greater than a particular limit but less than a time out time the pump continues to run for up to 30 minutes. If DC is greater than time out then a paused state 306 is entered.

At any time while in the operational state 308, the controller may be placed in the pause state 306 in response to a user input. Once the battery voltage reaches a low voltage cut off level or the lifetime of the pressure control apparatus has been reached, the controller de-activates the pressure control apparatus and an End of Life state is reached.

The controller 212 described with respect of the pressure control apparatus 200 of FIG. 3 operates in a similar manner as described above except that the initial pump-down and maintenance pump-down states are replaced with valve activation states in which the inlet 102 is coupled to the external source of negative pressure connected to the outlet 118 via controllable valve element 202.

Alternatively, the POST state 302 may be omitted.

The pressure control apparatus may be configured to be re-useable and be provided with a switch to allow the apparatus to be turned on and off as required. Such a re-usable apparatus may include rechargeable power cells, and may provide a low power indication in order to allow the power cells to be replaced/recharged.

In a disposable single use pressure control apparatus, activation may be provided by pulling an activation strip and it may not be possible to deactivate the apparatus once activated until the apparatus is to be discarded.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. An apparatus for applying negative pressure wound therapy, the apparatus comprising:
   a source of negative pressure configured to supply, via a fluid flow path, negative pressure to a wound covered by a wound dressing;
   a user interface configured to receive input from a user and provide operational status to the user;
   a controller; and
   a memory storing instructions that, when executed by the controller, cause the controller to:
   become active responsive to detection of an activation event;
   responsive to a first user input received via the user interface while the controller is active, activate the source of negative pressure to supply negative pressure to the wound; and
   become inactive responsive to determining that a lifetime threshold has been reached.

2. The apparatus of claim 1, wherein the activation event comprises removal of an activation strip or a press of a button of the user interface.

3. The apparatus of claim 1, wherein the first user input comprises a press of a button of the user interface.

4. The apparatus of claim 1, wherein the user interface comprises a plurality of visual indicators configured to provide to the user indications of a normal operation, a leak in the fluid flow path, and a low voltage of a power source.

5. The apparatus of claim 4, wherein the plurality of visual indicators is further configured to provide to the user an indication of a non-recoverable error.

6. The apparatus of claim 4, wherein the plurality of visual indicators comprises three separate visual indicators.

7. The apparatus of claim 1, wherein the instructions, when executed by the controller, cause the controller to:
   responsive to the first user input, activate the source of negative pressure source to attempt to establish a target level of negative pressure at the wound;
   responsive to a second user input received via the user interface, deactivate the source of negative pressure; and
   maintain negative pressure at the wound in a negative pressure range by alternately activating and deactivating the source of negative pressure.

8. The apparatus of claim 7, wherein the instructions, when executed by the controller, cause the controller to deactivate the source of negative pressure responsive to determining that the target level of negative pressure has been established.

9. The apparatus of claim 7, wherein the first user input and the second user input comprise a press of a button of the user interface.

10. The apparatus of claim 1, wherein the instructions, when executed by the controller, cause the controller to permanently deactivate the apparatus responsive to determining that the lifetime threshold has been reached.

11. The apparatus of claim 1, wherein the source of negative pressure and the wound dressing are configured to operate together to provide negative pressure wound therapy without use of a fluid collection canister.

12. An apparatus for applying negative pressure wound therapy, the apparatus comprising:
   a source of negative pressure configured to supply, via a fluid flow path, negative pressure to a wound covered by a wound dressing;
   a user interface configured to receive input from a user and provide operational status to the user;
   a controller; and
   a memory storing instructions that, when executed by the controller, cause the controller to:
   transition to an active state responsive to detection of an activation event;
   responsive to a first user input received via the user interface while the controller is in the active state, activate the source of negative pressure to supply negative pressure to the wound; and responsive to determining that a lifetime threshold has been reached, transition to an end of life state in which a transition to the active state is disallowed.

13. The apparatus of claim 12, wherein the activation event comprises removal of an activation strip or a press of a button of the user interface.

14. The apparatus of claim 12, wherein the first user input comprises a press of a button of the user interface.

15. The apparatus of claim 12, wherein the user interface comprises a plurality of visual indicators configured to provide to the user indications of a normal operation, a leak in the fluid flow path, and a low voltage of a power source.

16. The apparatus of claim 15, wherein the plurality of visual indicators is further configured to provide to the user an indication of a non-recoverable error.

17. The apparatus of claim 15, wherein the plurality of visual indicators comprises three separate visual indicators.

18. The apparatus of claim 12, wherein the instructions, when executed by the controller, cause the controller to:
responsive to the first user input, activate the source of negative pressure source to attempt to establish a target level of negative pressure at the wound;
responsive to a second user input received via the user interface, deactivate the source of negative pressure; and
maintain negative pressure at the wound in a negative pressure range by alternately activating and deactivating the source of negative pressure.

19. The apparatus of claim 18, wherein the instructions, when executed by the controller, cause the controller to deactivate the source of negative pressure responsive to determining that the target level of negative pressure has been established.

20. The apparatus of claim 18, wherein the first user input and the second user input comprise a press of a button of the user interface.

21. The apparatus of claim 12, wherein the source of negative pressure and the wound dressing are configured to operate together to provide negative pressure wound therapy without use of a fluid collection canister.

22. The apparatus of claim 12, wherein the instructions, when executed by the controller, cause the controller to:
operate the source of negative pressure for a number of retry cycles to attempt to establish a target level of negative pressure at the wound; and
pause operation of the source of negative pressure source responsive to determining that the target level of negative pressure at the wound has not been established as a result of operating the source of negative pressure source for the number of retry cycles.

23. A kit comprising the apparatus of claim 12 and the wound dressing.

* * * * *